US007670764B2

(12) United States Patent
Oh et al.

(10) Patent No.: US 7,670,764 B2
(45) Date of Patent: Mar. 2, 2010

(54) METHODS OF DIAGNOSING TISSUE FIBROSIS

(75) Inventors: Esther H. Oh, San Diego, CA (US); Catherine M. Smith, Carlsbad, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 561 days.

(21) Appl. No.: 10/971,195

(22) Filed: Oct. 22, 2004

(65) Prior Publication Data
US 2005/0186561 A1    Aug. 25, 2005

Related U.S. Application Data

(60) Provisional application No. 60/514,034, filed on Oct. 24, 2003.

(51) Int. Cl.
C12Q 1/04 (2006.01)
C12Q 1/70 (2006.01)
A61K 39/29 (2006.01)

(52) U.S. Cl. .......................... 435/5; 435/7.1; 424/228.1
(58) Field of Classification Search .................. 435/5; 424/228.1
See application file for complete search history.

(56) References Cited

U.S. PATENT DOCUMENTS

| 5,019,498 | A | 5/1991 | Chichibu |
| 6,218,129 | B1 | 4/2001 | Walsh et al. |
| 6,631,330 | B1 | 10/2003 | Poynard |
| 6,986,995 | B2 * | 1/2006 | Rose et al. ............ 435/7.1 |
| 7,141,380 | B2 | 11/2006 | Volker et al. |
| 2003/0175686 | A1 | 9/2003 | Rose et al. |
| 2007/0172907 | A1 | 7/2007 | Volker et al. |

FOREIGN PATENT DOCUMENTS

| EP | 0 911 343 | 4/1999 |
| EP | 1 150 123 | 10/2001 |
| WO | WO 01/86304 A2 | 11/2001 |
| WO | WO 03/073822 A2 | 9/2003 |
| WO | WO 03/087833 A2 | 10/2003 |

OTHER PUBLICATIONS

Website in Answer.com searches by Jul. 5, 2007 p. 1.*
Yokoyama et al. Am. J. Respri. Crit. Care Med. 1998, vol. 158, pp. 1680-1684.*
Callewaert et al., "Noninvasiv diagnosis of liver cirrhosis using DNA sequencer-based total serum protein glycomics", 2001, *Nature Medicine*, pp. 1-6.
Fortunato et al., "Multivariate Discriminant Function Based on Six Biochemical Markers in Blood Can Predict the Cirrhotic Evolution of Chronic Hepatitis", 2001, *Clinical Chemistry*, pp. 1696-1700, vol. 47(9).
Afdhal et al., *J. Hepatology*, 27: 993-1002 (1997).
Armstrong and Quigley, *Develop. Compar. Immunol.*, 23:375-390 (1999).
Arthur et al., *Alcohol Clin. Exp. Res.*, 23:940-943 (1999).
Bodden et al., *J. Bio. Chem.*, 269:18943-18952 (1994).
Boeker et al., *Clin Chim Acta*, 316:71-81 (2002).
Böker et al., *Hepato-Gastroenterol*, 47:812-819 (2000).
Bramley et al., *J. Hepatol.*, 13:8-13 (1991).
Brandt et al., *Acta Otolaryn.*, 442 (Suppl.):31-35 (1987).
Bray et al., *Am. Rev. Respir. Dis.*, 3:284-288 (1991).
Brophy et al., *Biochem. Biophys. Res. Comm.*, 167:898-903 (1990).
Castera et al., *J. Hepatol.*, 32:412-418 (2000).
Cawston et al., *Proteinase Inhibitors*, pp. 589-610 (1986).
Cazzolla et al., *Clinical Biochemistry*, 32:249-255 (1999).
Chichibu et al., *Clin. Chim. Acta*, 181:317-323 (1989).
Delpech et al., *Anal. Biochem.*, 149:555-565 (1985).
Docherty et al., *Nature*, 318:66-69 (1985).
Emlen et al., *J. Rheum.*, 23:974-978 (1996).
Engstrom-Laurent et al., *Scand. J. Clin. Lab. Invest.*, 45:497-504 (1985).
Fink et al., *J. Clin. Chem. Clin. Biochem.*, 27:261-276 (1989).
Gabrielli et al., *Clin. Chim. Acta*, 252:171-180 (1996).
Gabrielli et al., *Clin. Chim. Acta*, 265:21-31 (1997).
Ganrot, *Clin. Chim. Acta*, 14:493-501 (1966).
Goldberg et al., *Arthritis Rheum.*, 34:799-807 (1991).
Goldberg, *Anal. Biochem.*, 174:448-458 (1988).
Croft et al., *Br. J. Cancer*, 85:55-63 (2001).
Guechot et al., *Clin. Chem.*, 42:558-563 (1996).
Hakala et al., *J. Biol. Chem.*, 268:25803-25810 (1993).
Hall and Roberts, *Biochem. J.*, 171:27-38 (1978).
Imber and Pizzo, *J. Biol. Chem.*, 256:8134-8139 (1981).
Imbert-Bismut et al., *Lancet*, 357:1069-1075 (2001).
Janowska-Wieczorek et al., *Exp. Hematol.*, 28:1274-1285 (2000).
Jeffers et al., *Am. J. Gastroenterol.*, 90:1437-1440 (1995).
Johansen et al., *Scand. J. Gastroenterol.*, 32:582-590 (1997).
Johansen et al., *Br. J. Rheumatology*, 32:949-955 (1993).
Johansen et al., *J. Hepatol.*, 32:911-920 (2000).
Johansen et al., *J. Bone Miner. Res.*, 7:501-511 (1992).
Kasahara et al., *J Hepatol.*, 26:574-583 (1997).
Knodell et al., *Hepatology*, 1:431-435 (1981).
Kodama et al. *J. Immunol. Methods*, 127:103-108 (1990).
Konttinen et al., *Clin. Chimica Acta*, 193:39-47 (1990).
Kossakowska et al., *Amer. J. Pathology*, 153:1895-1902 (1998).

(Continued)

*Primary Examiner*—Gary Nickol
*Assistant Examiner*—Bao Qun Li
(74) *Attorney, Agent, or Firm*—Townsend and Townsend and Crew LLP

(57) ABSTRACT

The present invention provides a method of diagnosing the presence or severity of tissue fibrosis in an individual by detecting α2-macroglobulin (α2-MG) in a sample from the individual; detecting hyaluronic acid (HA) in a sample from the individual; detecting tissue inhibitor of metalloproteinases-1 (TIMP-1) in a sample from the individual; and diagnosing the presence or severity of tissue fibrosis in the individual based on the presence or level of α2-MG, HA and TIMP-1.

46 Claims, 5 Drawing Sheets

OTHER PUBLICATIONS

Kropf et al., *Clin. Chem.*, 34:2026-2030 (1988).
Laurent and Tengblad, *Anal. Biochemistry*, 109:386-394 (1980).
Li et al., *Conn. Tissue Res.*, 19:243-253 (1989).
Lindqvist et al., *Clin. Chem.*, 38:127-132 (1992).
Maingonnat and Delpech, *Ann. Clin. Biochem.*, 28:305-306 (1991).
McHutchison et al., *J. Gastroenterol. Hepatol.*, 15:945-951 (2000).
Murawaki et al., *Clin Chim Acta*, 218:47-58 (1993).
Murawaki et al. *J Gastroenterol*, 36:399-406 (2001).
Murphy et al., *Biochem. J.*, 195:167-170 (1981).
Murphy et al., *J Biol Chem*, 277(13):11069-11076 (2002).
Nyirkos and Golds, *Biochem. J.*, 268:265-268 (1990).
Oh et al., *Current Gastroenterology Reports*, 3:12-18 (2001).
Ortego et al., *Exp. Eye Res.*, 65:289-299 (1997).
Paramo et al., *Thromb. Haemost.*, 86:636-639 (2001).
Parra et al., *J. Vasc. Surg.*, 28:669-675 (1998).
Payan et al., *J. Chromatoqr.*, 566:9-18 (1991).
Pilette et al., *J. Hepatol.*, 28:439-446 (1998).
Pitsillides et al. *Arth. Rheum.*, 37:1030-1038 (1994).
Poole et al., *J. Biol. Chem.*, 260:6020-6025 (1985).
Poole et al., *Arth. Rheum.*, 33:790-799 (1990).
Poynard et al., *J. Viral Hepatitis*, 9:128-133 (2002).
Renkema et al., *Eur. J. Biochem.*, 251:504-509 (1998).
Rosenberg et al., *Hepatol.*, 34:396A, Abstract No. 895 (2001).
Saadeh et al., *Hepatology*, 33:196-200 (2001).
Sacco et al., *Cytokine*, 12:811-814 (2000).
Simon et al., *Cancer Res,.* 56:3112-3117 (1996).
Sottrup-Jensen, *The Plasma Proteins: Structure, Functional and Genetic Control*, Second edition, Orlando, pp. 191-291 (1987).
Stricklin, and Welgus, *J. Biol. Chem.*, 258:12252-12258 (1983).
The French Metavir Cooperative Study Group, *Hepatol.*, 20:15-20 (1994).
Ueno et al., *Gastroenterol.*, 105:475-481 (1993).
Verheijden et al., *Arthritis Rheum.*, 40:1115-1125 (1997).
Volck et al., *Proc. Assoc. Am. Physicians*, 110:351-360 (1998).
Walsh et al., *Diq Dis Sci*, 44:624-630 (1999).
Walsh et al., *J. Hepatol.*, 32:325-330 (2000).
Xuhuai et al., *Chinese Medical Journal*, 110:198-201 (1997).
Yoshiji et al., *Int. J. Cancer*, 69:131-134 (1996).
Friedman, S.L.; The cellular basis of hepatic fibrosis: Mechanism and treatment strategies; N Engl J Med 1993; 328: 1828-1835.
Friedman, S.L.; Molecular mechanism of hepatic fibrosis and principle of therapy; J Gastroenterol 1997; 32: 424-430 (abstract).
Hayasaka, S., et al.; Serum markers as tools to monitor liver fibrosis; Digestion 1998; 59: 381-384.
Murawaki, Y.; et al.; Serum markers for connective tissue turnover in patients with chronic hepatitis C: A comparative analysis; J. Hepatol 1995; 23: 145-152.
Naveau S.; et al.; Alpha-2 macroglobulin and hepatic fibrosis: diagnostic interest; Dig. Dis. Sci. 1994; 11: 2426-2432.
Oberti, F. et al.; Noninvasive diagnosis of hepatic fibrosis and cirrhosis; Gastroenterology 1997; 113: 1609-1616.
Poynard, T. et al.; A simple biological index for detection of alcoholic liver disease in drinkers; Gastroenterology 1991; 100: 1397-1402.
Teare, J.P. et al.; Comparison of serum procollagen III peptide concentrations and PGA index for assessment of hepatic fibrosis; The Lancet 1993; 342: 895-898.
Wong, V.S., et al.; Serum hyaluronic acid is a useful marker of liver fibrosis in chronic hepatitis C virus infection; J Viral Hepatitis 1998; 5: 187-192.
Schuppan, D.; Serum assays for liver fibrosis; Journal of Hepatology 1995; 22 (Suppl. 2) 82-88.
Friedman, S.L.; Molecular mechanism of hepatic fibrosis and principle of therapy; J Gastroenterol 1997; 32: 424-430.

* cited by examiner

```
   1 cccgccttcc tagctgtccc agtggagaag gaacaagcgc ctcactgcat ctgtgcaaac
  61 gggcggcaaa ctgtgtcctg ggcagtaacc ccaaagtcat taggaaatgt gaatttcact
 121 gtgagcgcag aggcactaga gtctcaagag ctgtgtggga ctgaggtgcc ttcagttcct
 181 gaacacggaa ggaaagacac agtcatcaag cctctgttgg ttgaacctga aggactagag
 241 aaggaaacaa cattcaactc cctactttgt ccatcaggtg gtgaggtttc tgaagaatta
 301 tccctgaaac tgccaccaaa tgtggtagaa gaatctgccc gagcttctgt ctcagttttg
 361 ggagacatat taggctctgc catgcaaaac acacaaaatc ttctccagat gccctatggc
 421 tgtggagagc agaatatggt cctctttgct cctaacatct atgtactgga ttatctaaat
 481 gaaacacagc agcttactcc agagatcaag tccaaggcca ttggctatct caacactggt
 541 taccagagac agttgaacta caaacactat gatggctcct acagcacctt tggggagcga
 601 tatggcagga accagggcaa cacctggctc acagcctttg ttctgaagac ttttgcccaa
 661 gctcgagcct acatcttcat cgatgaagca cacattaccc aagccctcat atggctctcc
 721 cagaggcaga aggacaatgg ctgtttcagg agctctgggt cactgctcaa caatgccata
 781 aagggaggag tagaagatga agtgaccctc tccgcctata tcaccatcgc ccttctggag
 841 attcctctca cagtcactca ccctgttgtc cgcaatgccc tgttttgcct ggagtcagcc
 901 tggaagacag cacaagaagg ggaccatggc agccatgtat ataccaaaga cctgctggcc
 961 tatgcttttg ccctggcagg taaccaggac aagaggaagg aagtactcaa gtcacttaat
1021 gaggaagctg tgaagaaaga caactctgtc cattgggagc gccctcagaa acccaaggca
1081 ccagtggggg atttttacga accccaggct ccctctgctg aggtggagat gacatcctat
1141 gtgctcctcg cttatctcac ggcccagcca gccccaacct cggaggacct gacctctgca
1201 accaacatcg tgaagtggat cacgaagcag cagaatgccc agggcggttt ctcctccacc
1261 caggacacag tggtggctct ccatgctctg tccaaatatg gagcagccac atttaccagg
1321 actgggaagg ctgcacaggt gactatccag tcttcaggga catttccag caaattccaa
1381 gtggacaaca caaccgcct gttactgcag caggtctcat gccagagct gcctggggaa
1441 tacagcatga agtgacagg agaaggatgt gtctacctcc agacatcctt gaaatacaat
1501 attctcccag aaaaggaaga gttcccctt gctttaggag tgcagactct gcctcaaact
1561 tgtgatgaac ccaaagccca caccagctc caaatctccc taagtgtcag ttacacaggg
1621 agccgctctg cctccaacat ggcgatcgtt gatgtgaaga tggtctctgg cttcattccc
1681 ctgaagccaa cagtgaaaat gcttgaaaga tctaaccatg tgagccggac agaagtcagc
1741 agcaaccatg tcttgattta ccttgataag gtgtcaaatc agacactgag cttgttcttc
1801 acggttctgc aagatgtccc agtaagagat ctgaaaccag ccatagtgaa agtctatgat
1861 tactacgaga cggatgagtt tgcaattgct gagtacaatg ctccttgcag caaagatctt
1921 ggaaatgctt gaagaccaca aggctgaaaa gtgctttgct ggagtcctgt tctcagagct
1981 ccacagaaga cacgtgtttt tgtatcttta aagacttgat gaataaacac ttttctggt
2041 c
```

A

PAFLAVPVEKEQAPHCICANGRQTVSWAVTPKSLGNVNFTVSAEALESQELCGTEVPSVPEHGRKDTVIKPL
LVEPEGLEKETTFNSLLCPSGGEVSEELSLKLPPNVVEESARASVSVLGDILGSAMQNTQNLLQMPYGCGEQ
NMVLFAPNIYVLDYLNETQQLTPEIKSKAIGYLNTGYQRQLNYKHYDGSYSTFGERYGRNQGNTWLTAFVLK
TFAQARAYIFIDEAHITQALIWLSQRQKDNGCFRSSGSLLNNAIKGGVEDEVTLSAYITIALLEIPLTVTHP
VVRNALFCLESAWKTAQEGDHGSHVYTKDLLAYAFALAGNQDKRKEVLKSLNEEAVKKDNSVHWERPQKPKA
PVGDFYEPQAPSAEVEMTSYVLLAYLTAQPAPTSEDLTSATNIVKWITKQQNAQGGFSSTQDTVVALHALSK
YGAATFTRTGKAAQVTIQSSGTFSSKFQVDNNNRLLLQQVSLPELPGEYSMKVTGEGCVYLQTSLKYNILPE
KEEFPFALGVQTLPQTCDEPKAHTSFQISLSVSYTGSRSASNMAIVDVKMVSGFIPLKPTVKMLERSNHVSR
TEVSSNHVLIYLDKVSNQTLSLFFTVLQDVPVRDLKPAIVKVYDYYETDEFAIAEYNAPCSKDLGNA

```
  1 aggggcctta gcgtgccgca tcgccgagat ccagcgccca gagagacacc agagaaccca
 61 ccatggcccc ctttgagccc ctggcttctg gcatcctgtt gttgctgtgg ctgatagccc
121 ccagcagggc ctgcacctgt gtcccacccc acccacagac ggccttctgc aattccgacc
181 tcgtcatcag ggccaagttc gtggggacac cagaagtcaa ccagaccacc ttataccagc
241 gttatgagat caagatgacc aagatgtata aaggggttcca agccttaggg gatgccgctg
301 acatccggtt cgtctacacc cccgccatgg agagtgtctg cggatacttc cacaggtccc
361 acaaccgcag cgaggagttt ctcattgctg gaaaactgca ggatggactc ttgcacatca
421 ctacctgcag tttcgtggct ccctggaaca gcctgagctt agctcagcgc cggggcttca
481 ccaagaccta cactgttggc tgtgaggaat gcacagtgtt ccctgtttta tccatcccct
541 gcaaactgca gagtggcact cattgcttgt ggacggacca gctcctccaa ggctctgaaa
601 agggcttcca gtcccgtcac cttgcctgcc tgcctcggga gccagggctg tgcacctggc
661 agtccctgcg gtcccagata gcctgaatcc tgcccggagt ggaactgaag cctgcacagt
721 gtccaccctg ttcccactcc catctttctt ccggacaatg aaataaagag ttaccaccca
781 gc
```

A

MAPFEPLASGILLLLWLIAPSRACTCVPPHPQTAFCNSDLVIRAKFVGTPEVNQTTLYQRYEIKMTKMY
KGFQALGDAADIRFVYTPAMESVCGYFHRSHNRSEEFLIAGKLQDGLLHITTCSFVAPWNSLSLAQRRG
FTKTYTVGCEECTVFPCLSIPCKLQSGTHCLWTDQLLQGSEKGFQSRHLACLPREPGLCTWQSLRSQIA

SEQUENCE LISTING

<160> NUMBER OF SEQ ID NOS: 4

<210> SEQ ID NO 1
<211> LENGTH: 2041
<212> TYPE: DNA
<213> ORGANISM: Homo sapiens
<220> FEATURE:
<223> OTHER INFORMATION: mature human alpha-2-macroglobulin (alpha2-MG) cDNA 3' end
<220> FEATURE:
<221> NAME/KEY: CDS
<222> LOCATION: (1)..(1932)
<223> OTHER INFORMATION: mature human alpha-2-macroglobulin (alpha2-MG)

<400> SEQUENCE: 1

```
cccgccttcc tagctgtccc agtggagaag gaacaagcgc ctcactgcat ctgtgcaaac      60
gggcggcaaa ctgtgtcctg ggcagtaacc ccaaagtcat taggaaatgt gaatttcact     120
gtgagcgcag aggcactaga gtctcaagag ctgtgtggga ctgaggtgcc ttcagttcct     180
gaacacggaa ggaaagacac agtcatcaag cctctgttgg ttgaacctga aggactagag     240
aaggaaacaa cattcaactc cctactttgt ccatcaggtg gtgaggtttc tgaagaatta     300
tccctgaaac tgccaccaaa tgtggtagaa gaatctgccc gagcttctgt ctcagttttg     360
ggagacatat taggctctgc catgcaaaac acacaaaatc ttctccagat gccctatggc     420
tgtggagagc agaatatggt cctctttgct cctaacatct atgtactgga ttatctaaat     480
gaaacacagc agcttactcc agagatcaag tccaaggcca ttggctatct caacactggt     540
taccagagac agttgaacta caaacactat gatggctcct acagcacctt gggggagcga     600
tatggcagga accagggcaa cacctggctc acagcctttg ttctgaagac ttttgcccaa     660
gctcgagcct acatcttcat cgatgaagca cacattaccc aagccctcat atggctctcc     720
cagaggcaga aggacaatgg ctgtttcagg agctctgggt cactgctcaa caatgccata     780
aagggaggag tagaagatga agtgaccctc tccgcctata tcaccatcgc ccttctggag     840
attcctctca cagtcactca ccctgttgtc cgcaatgccc tgttttgcct ggagtcagcc     900
tggaagacag cacaagaagg ggaccatggc agccatgtat ataccaaaga cctgctggcc     960
tatgcttttg ccctggcagg taaccaggac aagaggaagg aagtactcaa gtcacttaat    1020
gaggaagctg tgaagaaaga caactctgtc cattgggagc ccctcagaa acccaaggca    1080 ccagtggggg attttacga accccaggct ccctctgctg aggtggagat gacatccctat    1140 gtgctcctcg cttatctcac ggcccagcca gccccaacct cggaggacct gacctctgca    1200
accaacatcg tgaagtggat cacgaagcag cagaatgccc agggcggttt ctcctccacc    1260
caggacacag tggtggctct ccatgctctg tccaaatatg gagcagccac atttaccagg    1320
actgggaagg ctgcacaggt gactatccag tcttcaggga catttttccag caaattccaa    1380 gtggacaaca caaccgcct gttactgcag caggtctcat tgccagagct gcctggggaa    1440
tacagcatga aagtgacagg agaaggatgt gtctacctcc agacatcctt gaaatacaat    1500
attctcccag aaaaggaaga gttccccttt gctttaggag tgcagactct gcctcaaact    1560
tgtgatgaac ccaaagccca caccagcttc caaatctccc taagtgtcag ttacacaggg    1620
```

-continued

```
agccgctctg cctccaacat ggcgatcgtt gatgtgaaga tggtctctgg cttcattccc    1680
ctgaagccaa cagtgaaaat gcttgaaaga tctaaccatg tgagccggac agaagtcagc    1740
agcaaccatg tcttgattta ccttgataag gtgtcaaatc agacactgag cttgttcttc    1800
acggttctgc aagatgtccc agtaagagat ctgaaaccag ccatagtgaa agtctatgat    1860
tactacgaga cggatgagtt tgcaattgct gagtacaatg ctccttgcag caaagatctt    1920
ggaaatgctt gaagaccaca aggctgaaaa gtgctttgct ggagtcctgt tctcagagct    1980
ccacagaaga cacgtgtttt tgtatcttta aagacttgat gaataaacac ttttctggt     2040 c                                                                    2041

<210> SEQ ID NO 2
<211> LENGTH: 643
<212> TYPE: PRT
<213> ORGANISM: Homo sapiens
<220> FEATURE:
<223> OTHER INFORMATION: mature human alpha-2-macroglobulin (alpha2-MG)

<400> SEQUENCE: 2

Pro Ala Phe Leu Ala Val Pro Val Glu Lys Glu Gln Ala Pro His Cys
  1               5                  10                  15

Ile Cys Ala Asn Gly Arg Gln Thr Val Ser Trp Ala Val Thr Pro Lys
             20                  25                  30

Ser Leu Gly Asn Val Asn Phe Thr Val Ser Ala Glu Ala Leu Glu Ser
         35                  40                  45

Gln Glu Leu Cys Gly Thr Glu Val Pro Ser Val Pro Glu His Gly Arg
     50                  55                  60

Lys Asp Thr Val Ile Lys Pro Leu Leu Val Glu Pro Glu Gly Leu Glu
 65                  70                  75                  80

Lys Glu Thr Thr Phe Asn Ser Leu Leu Cys Pro Ser Gly Gly Glu Val
                 85                  90                  95

Ser Glu Glu Leu Ser Leu Lys Leu Pro Pro Asn Val Val Glu Glu Ser
            100                 105                 110

Ala Arg Ala Ser Val Ser Val Leu Gly Asp Ile Leu Gly Ser Ala Met
        115                 120                 125

Gln Asn Thr Gln Asn Leu Leu Gln Met Pro Tyr Gly Cys Gly Glu Gln
    130                 135                 140

Asn Met Val Leu Phe Ala Pro Asn Ile Tyr Val Leu Asp Tyr Leu Asn
145                 150                 155                 160

Glu Thr Gln Gln Leu Thr Pro Glu Ile Lys Ser Lys Ala Ile Gly Tyr
                165                 170                 175

Leu Asn Thr Gly Tyr Gln Arg Gln Leu Asn Tyr Lys His Tyr Asp Gly
            180                 185                 190

Ser Tyr Ser Thr Phe Gly Glu Arg Tyr Gly Arg Asn Gln Gly Asn Thr
        195                 200                 205

Trp Leu Thr Ala Phe Val Leu Lys Thr Phe Ala Gln Ala Arg Ala Tyr
    210                 215                 220

Ile Phe Ile Asp Glu Ala His Ile Thr Gln Ala Leu Ile Trp Leu Ser
225                 230                 235                 240

Gln Arg Gln Lys Asp Asn Gly Cys Phe Arg Ser Ser Gly Ser Leu Leu
                245                 250                 255

Asn Asn Ala Ile Lys Gly Gly Val Glu Asp Glu Val Thr Leu Ser Ala
            260                 265                 270

Tyr Ile Thr Ile Ala Leu Leu Glu Ile Pro Leu Thr Val Thr His Pro
```

```
                275                 280                 285
Val Val Arg Asn Ala Leu Phe Cys Leu Glu Ser Ala Trp Lys Thr Ala
    290                 295                 300
Gln Glu Gly Asp His Gly Ser His Val Tyr Thr Lys Asp Leu Leu Ala
305                 310                 315                 320
Tyr Ala Phe Ala Leu Ala Gly Asn Gln Asp Lys Arg Lys Glu Val Leu
                325                 330                 335
Lys Ser Leu Asn Glu Glu Ala Val Lys Lys Asp Asn Ser Val His Trp
                340                 345                 350
Glu Arg Pro Gln Lys Pro Lys Ala Pro Val Gly Asp Phe Tyr Glu Pro
            355                 360                 365
Gln Ala Pro Ser Ala Glu Val Glu Met Thr Ser Tyr Val Leu Leu Ala
            370                 375                 380
Tyr Leu Thr Ala Gln Pro Ala Pro Thr Ser Glu Asp Leu Thr Ser Ala
385                 390                 395                 400
Thr Asn Ile Val Lys Trp Ile Thr Lys Gln Gln Asn Ala Gln Gly Gly
                405                 410                 415
Phe Ser Ser Thr Gln Asp Thr Val Val Ala Leu His Ala Leu Ser Lys
                420                 425                 430
Tyr Gly Ala Ala Thr Phe Thr Arg Thr Gly Lys Ala Ala Gln Val Thr
            435                 440                 445
Ile Gln Ser Ser Gly Thr Phe Ser Ser Lys Phe Gln Val Asp Asn Asn
450                 455                 460
Asn Arg Leu Leu Leu Gln Gln Val Ser Leu Pro Glu Leu Pro Gly Glu
465                 470                 475                 480
Tyr Ser Met Lys Val Thr Gly Glu Gly Cys Val Tyr Leu Gln Thr Ser
                485                 490                 495
Leu Lys Tyr Asn Ile Leu Pro Glu Lys Glu Phe Pro Phe Ala Leu
                500                 505                 510
Gly Val Gln Thr Leu Pro Gln Thr Cys Asp Glu Pro Lys Ala His Thr
            515                 520                 525
Ser Phe Gln Ile Ser Leu Ser Val Ser Tyr Thr Gly Ser Arg Ser Ala
            530                 535                 540
Ser Asn Met Ala Ile Val Asp Val Lys Met Val Ser Gly Phe Ile Pro
545                 550                 555                 560
Leu Lys Pro Thr Val Lys Met Leu Glu Arg Ser Asn His Val Ser Arg
                565                 570                 575
Thr Glu Val Ser Ser Asn His Val Leu Ile Tyr Leu Asp Lys Val Ser
                580                 585                 590
Asn Gln Thr Leu Ser Leu Phe Phe Thr Val Leu Gln Asp Val Pro Val
            595                 600                 605
Arg Asp Leu Lys Pro Ala Ile Val Lys Val Tyr Asp Tyr Tyr Glu Thr
610                 615                 620
Asp Glu Phe Ala Ile Ala Glu Tyr Asn Ala Pro Cys Ser Lys Asp Leu
625                 630                 635                 640
Gly Asn Ala
```

<210> SEQ ID NO 3
<211> LENGTH: 782
<212> TYPE: DNA
<213> ORGANISM: Homo sapiens
<220> FEATURE:
<223> OTHER INFORMATION: human tissue inhibitor of metalloproteinase-1
      (TIMP-1) cDNA
<220> FEATURE:

```
<221> NAME/KEY: CDS
<222> LOCATION: (63)..(686)
<223> OTHER INFORMATION: human tissue inhibitor of metalloproteinase-1
      (TIMP-1)

<400> SEQUENCE: 3 agggggcctta gcgtgccgca tcgccgagat ccagcgccca gagagacacc agagaaccca    60
ccatggcccc ctttgagccc ctggcttctg gcatcctgtt gttgctgtgg ctgatagccc   120
ccagcagggc ctgcacctgt gtcccacccc acccacagac ggccttctgc aattccgacc   180
tcgtcatcag ggccaagttc gtggggacac cagaagtcaa ccagaccacc ttataccagc   240
gttatgagat caagatgacc aagatgtata aagggttcca agccttaggg gatgccgctg   300
acatccggtt cgtctacacc cccgccatgg agagtgtctg cggatacttc cacaggtccc   360
acaaccgcag cgaggagttt ctcattgctg gaaaactgca ggatggactc ttgcacatca   420
ctacctgcag tttcgtggct ccctggaaca gcctgagctt agctcagcgc cggggcttca   480
ccaagaccta cactgttggc tgtgaggaat gcacagtgtt ccctgtttta tccatcccct   540
gcaaactgca gagtggcact cattgcttgt ggacggacca gctcctccaa ggctctgaaa   600
agggcttcca gtcccgtcac cttgcctgcc tgcctcggga gccagggctg tgcacctggc   660
agtccctgcg gtcccagata gcctgaatcc tgcccggagt ggaactgaag cctgcacagt   720
gtccaccctg ttcccactcc catctttctt ccggacaatg aaataaagag ttaccaccca   780
gc                                                                   782

<210> SEQ ID NO 4
<211> LENGTH: 207
<212> TYPE: PRT
<213> ORGANISM: Homo sapiens
<220> FEATURE:
<223> OTHER INFORMATION: human tissue inhibitor of metalloproteinase-1
      (TIMP-1)

<400> SEQUENCE: 4

Met Ala Pro Phe Glu Pro Leu Ala Ser Gly Ile Leu Leu Leu Leu Trp
 1               5                  10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175
```

-continued

```
Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
            195                 200                 205
```

METHODS OF DIAGNOSING TISSUE FIBROSIS

CROSS-REFERENCES TO RELATED APPLICATIONS

This application claims the benefit of U.S. Provisional Application No. 60/514,034, filed Oct. 24, 2003, which is herein incorporated by reference for all purposes.

FIELD OF THE INVENTION

The present invention relates generally to the field fibrosis and, more specifically, to a panel of serological markers which together are diagnostic of tissue fibrosis.

BACKGROUND OF THE INVENTION

Progressive fibrosis of the liver, kidney, lungs and other organs frequently results in organ failure that leads to organ transplantation or death, affecting millions in the United States and worldwide. Hepatic fibrosis, for example, is the leading non-malignant gastrointestinal cause of death in the United States, and the progression of fibrosis is the single most important determinant of morbidity and mortality in patients with chronic liver disease. Furthermore, the process of fibrosis is common to liver diseases of many etiologies, including chronic viral hepatitis B and C, autoimmune liver disease such as autoimmune hepatitis, alcoholic liver disease, fatty liver disease; primary biliary cirrhosis; and drug-induced liver disease. The fibrosis seen in these disorders results from chronic insults to the liver such as viral infection, alcohol or drugs.

Hepatitis C, for example, is one of the leading causes of chronic liver disease in the United States, where an estimated 3.9 million people are chronically infected with hepatitis C virus (HCV) and approximately 30,000 new cases of acute HCV occur each year (Alter, *Semin. Liver Dis.* 15:5-14 (1995)). The prevalence of hepatitis C is estimated to be 1.8% in the United States, with up to 10,000 deaths per year likely resulting from chronic hepatitis C infection (Alter, supra, 1995).

While hepatic fibrosis is a reversible process resulting in the accumulation of extracellular matrix, liver cirrhosis is an irreversible process characterized by thick bands of matrix which completely encircle the parenchyma to form nodules. Untreated, fibrosis of the liver leads to cirrhosis and eventually end-stage liver disease or cancer. Cirrhosis of the liver is a common condition that frequently goes undetected. For example, in a large sample of the general Danish population, the prevalence of liver cirrhosis was 4.5%, of which one-third were undiagnosed at the time of death (Graudal, *J. Intern. Med.* 230:165-171 (1991)).

Timely and accurate diagnosis of liver fibrosis is important to effective medical treatment. As an example, patients with hepatitis C and cirrhosis are less likely to respond to treatment with α-interferon compared to patients with less advanced disease (Davis, *Hepatology* 26(Supp. 1):122-127S). Similarly, treatments for chronic HCV infection can be contraindicated in patients with histologically advanced and decompensated disease (NIH Consensus Development Conference Panel Statement, *Hepatology* 26 (Suppl. 1):25-105S (1997)). The importance of early diagnosis is further emphasized by the serious early complications such as variceal rupture that are associated with cirrhosis; these complications can be prevented by early detection of cirrhosis (Cals and Pasqual, *Gastroenterol. Clin. Biol.* 12:245-254 (1988)).

Diagnosis of the presence or severity of fibrotic liver disease is difficult, with liver biopsy currently the most reliable method available. Unfortunately, liver biopsy has several limitations: pain in about 30% of patients; the risk of severe complications such as hemorrhage or infection; a death rate of 3 in 10,000; and the cost of hospitalization (Nord, *Gastrointest. Endosc.* 28:102-104 (1982); Cadranel et al., *Hepatology* 32:47-481 (2000); and Poynard et al., *Can. J. Gastroenterol.* 14:543-548 (2000)). Furthermore, slowly progressive diseases such as hepatitis C require repeated biopsies for continual assessment of disease progression, thus compounding the risks and costs of the procedure. Finally, biopsy can fail to detect disease because of the heterogeneous distribution of pathological changes in the liver; it is not surprising, then, that false negatives are seen in a significant percentage of cases biopsied (Nord, supra, 1982).

For years there has been a search for biochemical or serological markers which reflect fibrotic processes in liver disease and which can serve as a surrogate for liver biopsy. Serological markers for other fibrotic diseases are also of tremendous clinical value. However, the performance of any single marker has not been good enough to substitute for the biopsy procedure in detecting or staging fibrosis. Thus, there is a need for a non-invasive method of diagnosing the presence or severity of liver fibrosis, and other tissue fibrosis. The present invention satisfies this need by providing a convenient and reliable method for detection of liver fibrosis and other tissue fibrosis that is suitable for serial testing. Related advantages are provided as well.

BRIEF SUMMARY OF THE INVENTION

The present invention provides methods for diagnosing and for determining the severity of tissue fibrosis.

In one aspect the invention provides a method for diagnosing the presence or severity of tissue fibrosis in an individual, by obtaining a sample from the individual and determining the levels of markers of fibrosis, e.g., α2-macroglobulin (α2MG or A2M), hyaluronic acid (HA), tissue inhibitor of metalloproteinases-1 (TIMP-1). An algorithm is then used to determine an index value for the individual based upon an α2-macroglobulin, HA, and TIMP-1 levels; and the index value is used to diagnosing the presence or severity of tissue fibrosis in the individual.

In one embodiment, an index cutoff value is used to determine the presence or severity of tissue fibrosis. The index cutoff value can be, for example, between 0.2 and 0.7 or between 0.3 and 0.6. An iterative approach can be used where multiple algorithms or index cutoffs values are used to analyze a sample or samples from an individual. For example, a second index cutoff value can be based upon the α2-macroglobulin, HA, and TIMP-1 level algorithm, or a level of an additional marker of fibrosis is determined and used to determine a second index value for the individual based upon a second algorithm and a second index cutoff value is based upon the second algorithm.

In one embodiment, a level of at most three markers of fibrosis is determined for use in the invention. In another embodiment, a level of at least three markers of fibrosis is determined for use in the invention. For example, levels of four, five, or six markers of fibrosis can be determined.

In one embodiment, an algorithm is selected such that fewer than 25%, 20%, 15%, 10% or 5% indeterminate values are obtained. In a preferred embodiment, an algorithm is selected such that no indeterminate values are obtained.

In addition to α2MG, HA, and TIMP-1 levels; the levels of other markers of fibrosis can be determined. Additional markers of fibrosis include PIIINP; laminin; tenascin; collagen type IV; collagen type VI; YKL-40, MMP-3; MMP-2; MMP-9/TIMP-1 complex; sFas ligand; TGF-β1; IL-10; apoA1; apoA2; apoB; integrin 1β; TNF-alpha; MCP-1; leptin; VEGF; PDGF; collagen type I; collagen type XIV; fibronectin; prolyl hydroxylase; nitrotyrosine; nitic oxide; MDA, 4HNE, or LPO; F2-isoprostanes, 8-epi-PGF-2alpha; β-hydroxybutyrate; IGF-1; IGFBP3; and liver FABP. One or more additional markers of fibrosis can be chosen for use in the invention.

In another aspect, the tissue fibrosis is liver fibrosis. In one embodiment the following algorithm is used to diagnose the presence or severity of liver fibrosis:

$$\text{Index} = \frac{\text{Exp}^{[-4.3633+(0.0108*\text{HA ng/ml})+(0.0015*\text{TIMP-1 ng/ml})+(0.5357*\text{A2M mg/ml})]}}{1+\text{Exp}^{[-4.3633+(0.0108*\text{HA ng/ml})+(0.0015*\text{TIMP-1 ng/ml})+(0.5357*\text{A2M mg/ml})]}}$$

In a further embodiment, the index cutoff value is 0.42 and an index value greater than 0.42 correlates with moderate/severe liver fibrosis. In another embodiment the individual has viral hepatitis, e.g., infection with hepatitis C virus, hepatitis B virus, or hepatitis A virus. In yet another embodiment, the individual is co-infected with at least two viruses, including for example one or more of the following: hepatitis A, hepatitis B, hepatitis C, and HIV-1. Other liver disease are encompassed by the invention, e.g., autoimmune liver disease, alcoholic liver disease, fatty liver disease, drug-induced liver disease, and primary biliary cirrhosis.

The level of α2-MG protein can be determined using an α2-MG-specific binding agent, e.g., anti-α2-MG antibody, or can be determined using analysis of α2-MG activity. The level of HA can be determined using an HA-specific binding agent, e.g., an HA-binding protein or an anti-HA antibody. The level of TIMP-1 protein can be determined using an TIMP-1-specific binding agent, e.g., an anti-TIMP-1 antibody or can be determined using analysis of TIMP-1 activity. The level of α2-MG protein, HA and TIMP-1 protein can each be determined using an enzyme-linked assay.

In one embodiment, the methods of the invention are performed using a single sample obtained from the individual. The sample can be, for example, from blood, serum, plasma, urine, saliva, and liver tissue or other organ tissue. In a preferred embodiment, the sample is a serum sample.

In a preferred embodiment, the methods of the invention are used to differentiate between no or mild liver fibrosis and moderate to severe liver fibrosis.

In another aspect, the invention provides methods for differentiating no or mild tissue fibrosis from moderate to severe tissue fibrosis in an individual by contacting an appropriate dilution of a sample from said individual with anti-α2-MG antibody to form a first complex of α2-MG and anti-α2-MG antibody and determine the amount of α2-MG-containing first complex; contacting an appropriate dilution of a sample from said individual with a HA-binding protein (HABP) under conditions suitable to form a second complex of HA and HABP and determine the amount of HA-containing second complex; contacting an appropriate dilution of a sample from said individual with anti-TIMP-1 antibody to form a third complex of TIMP-1 and anti-TIMP-1 antibody and determine the amount of TIMP-1-containing third complex; determining an index value for the individual based upon an α2-macroglobulin, HA, and TIMP-1 complex amount algorithm; and differentiating no or mild tissue fibrosis from moderate or severe tissue fibrosis in said individual based on the index value. In one embodiment, an index cutoff value is determined and used to differentiate no or mild tissue fibrosis from moderate or severe tissue fibrosis. In other embodiments, the complexes are optionally washed to remove unbound molecules. In a preferred embodiment, the tissue fibrosis is liver fibrosis.

In another aspect, the invention provides a method for monitoring the efficacy of anti-fibrotic therapy in a patient by obtaining a sample from the individual and determining the levels of markers of fibrosis, e.g., α2-macroglobulin (α2MG or A2M), hyaluronic acid (HA), tissue inhibitor of metalloproteinases-1 (TIMP-1). An algorithm is then used to determine an index value for the individual based upon an α2-macroglobulin, HA, and TIMP-1 levels; and the index value is used to diagnosing the presence or severity of tissue fibrosis in the individual. In one embodiment, the presence or severity of tissue fibrosis is compared to a determination of the presence or severity of tissue fibrosis in the individual at an earlier time.

In one embodiment, an index cutoff value is used to determine the presence or severity of tissue fibrosis.

In one embodiment, a level of at most three markers of fibrosis is determined for use in the invention. In another embodiment, a level of at least three markers of fibrosis is determined for use in the invention. For example, levels of four five or six markers of fibrosis can be determined.

In addition to α2MG, HA, and TIMP-1 levels; the levels of other markers of fibrosis can be detemined. Additional markers of fibrosis include PIIINP; laminin; tenascin; collagen type IV; collagen type VI; YKL-40, MMP-3; MMP-2; MMP-9/TIMP-1 complex; sFas ligand; TGF-β1; IL-10; apoA1; apoA2; apoB; integrin 1β; TNF-alpha; MCP-1; leptin; VEGF; PDGF; collagen type I; collagen type XIV; fibronectin; prolyl hydroxylase; nitrotyrosine; nitic oxide; MDA, 4HNE, or LPO; F2-isoprostanes, 8-epi-PGF-2alpha; β-hydroxybutyrate; IGF-1; IGFBP3; and liver FABP. One or more additional markers of fibrosis can be chosen for use in the invention.

In another aspect, the tissue fibrosis is liver fibrosis.

In one embodiment, the level of α2-MG protein is determined using an anti-α2-MG antibody. In another embodiment, the level of HA is determined using an HA-binding protein. In yet another embodiment, the level of TIMP-1 protein is determined using an anti-TIMP-1 antibody.

In another embodiment the invention provides a method of differentiating no/mild liver fibrosis from moderate/severe liver fibrosis in an individual by obtaining a sample from the individual and determining the levels of markers of fibrosis, e.g., α2-macroglobulin (α2MG or A2M), hyaluronic acid (HA), tissue inhibitor of metalloproteinases-1 (TIMP-1). An algorithm is then used to determine an index value for the individual based upon an α2-macroglobulin, HA, and TIMP-1 levels; and the index value is compared to an index cutoff value of 0.42, where the individual is diagnosed as having moderate/severe liver fibrosis when the index value is above the index cutoff value of 0.42.

In one embodiment, the individual has a disorder such as viral hepatitis, autoimmune liver disease, alcoholic liver disease, fatty liver disease and drug-induced liver disease or is infected with a virus, e.g., hepatitis A, hepatitis B, or hepatitis C virus. Samples can be taken from blood, serum, plasma, urine, saliva and liver tissue. In a preferred embodiment the α2-MG, level, HA level and TIMP-1 level each are determined in a serum sample.

In another embodiment, the individual has nonalcoholic steatohepatitis (NASH) and the index cutoff value is 0.475.

In another aspect the invention provides a method for monitoring the progression of tissue fibrosis in an individual, by obtaining a sample from the individual and determining the levels of markers of fibrosis, e.g., α2-macroglobulin (α2MG or A2M), hyaluronic acid (HA), tissue inhibitor of metalloproteinases-1 (TIMP-1). An algorithm is then used to determine an index value for the individual based upon an α2-macroglobulin, HA, and TIMP-1 levels; and the index value is used to diagnosing the presence or severity of tissue fibrosis in the individual. In one embodiment, the presence or severity of tissue fibrosis is compared to a determination of the presence or severity of tissue fibrosis in the individual at an earlier time.

In one embodiment, an index cutoff value is used to determine the presence or severity of tissue fibrosis.

In one embodiment, a level of at most three markers of fibrosis is determined for use in the invention. In another embodiment, a level of at least three markers of fibrosis is determined for use in the invention. For example, levels of four five or six markers of fibrosis can be determined.

In addition to α2MG, HA, and TIMP-1 levels; the levels other markers of fibrosis can be detemined. Additional markers of fibrosis include PIIINP; laminin; tenascin; collagen type IV; collagen type VI; YKL-40, MMP-3; MMP-2; MMP-9/TIMP-1 complex; sFas ligand; TGF-β1; IL-10; apoA1; apoA2; apoB; integrin 1β; TNF-alpha; MCP-1; leptin; VEGF; PDGF; collagen type I; collagen type XIV; fibronectin; prolyl hydroxylase; nitrotyrosine; nitic oxide; MDA, 4HNE, or LPO; F2-isoprostanes, 8-epi-PGF-2alpha; β-hydroxybutyrate; IGF-1; IGFBP3; and liver FABP. One or more additional markers of fibrosis can be chosen for use in the invention.

In another aspect, the tissue fibrosis is liver fibrosis.

In one embodiment, the level of α2-MG protein is determined using an anti-α2-MG antibody. In another embodiment, the level of HA is determined using an HA-binding protein. In yet another embodiment, the level of TIMP-1 protein is determined using an anti-TIMP-1 antibody.

In another aspect the invention provides, a method of monitoring a response to a therapeutic agent in an individual in need of such agent by obtaining a sample from the individual and determining the levels of markers of fibrosis, e.g., α2-macroglobulin (α2MG or A2M), hyaluronic acid (HA), tissue inhibitor of metalloproteinases-1 (TIMP-1). An algorithm is then used to determine an index value for the individual based upon an α2-macroglobulin, HA, and TIMP-1 levels; and the index value is used to diagnosing the presence or severity of tissue fibrosis in the individual. In one embodiment, the presence or severity of tissue fibrosis is compared to a determination of the presence or severity of tissue fibrosis in the individual at an earlier time.

In one embodiment, an index cutoff value is used to determine the presence or severity of tissue fibrosis.

In one embodiment, a level of at most three markers of fibrosis is determined for use in the invention. In another embodiment, a level of at least three markers of fibrosis is determined for use in the invention. For example, levels of four five or six markers of fibrosis can be determined.

In addition to α2MG, HA, and TIMP-1 levels; the levels of other markers of fibrosis can be determined. Additional markers of fibrosis include PIIINP; laminin; tenascin; collagen type IV; collagen type VI; YKL-40, MMP-3; MMP-2; MMP-9/TIMP-1 complex; sFas ligand; TGF-β1; IL-10; apoA1; apoA2; apoB; integrin 1β; TNF -alpha; MCP-1; leptin; VEGF; PDGF; collagen type I; collagen type XIV; fibronectin; prolyl hydroxylase; nitrotyrosine; nitic oxide; MDA, 4HNE, or LPO; F2-isoprostanes, 8-epi-PGF-2alpha; β-hydroxybutyrate; IGF-1; IGFBP3; and liver FABP. One or more additional markers of fibrosis can be chosen for use in the invention.

In another aspect, the tissue fibrosis is liver fibrosis.

In one embodiment, the level of α2-MG protein is determined using an anti-α2-MG antibody. In another embodiment, the level of HA is determined using an HA-binding protein. In yet another embodiment, the level of TIMP-1 protein is determined using an anti-TIMP-1 antibody.

In one embodiment a response to a therapeutic agent is determined in an individual with a viral disease, e.g., hepatitis A, hepatitis B, hepatitis C, or HIV-1.

In another embodiment, the therapeutic agent is an antifibrotic agent. In yet another embodiment, the therapeutic agent is an anti-viral agent.

BRIEF DESCRIPTION OF THE DRAWINGS

FIG. 1 shows the nucleic acid sequence (SEQ ID NO: 1) and corresponding amino acid sequence (SEQ ID NO: 2) for mature human α2-macroglobulin available from Genbank accession M36501.

FIG. 2 shows the nucleic acid sequence (SEQ ID NO: 3) and corresponding amino acid sequence (SEQ ID NO: 4) for human tissue inhibitor of metalloproteinases-1 (TIMP-1) available from Genbank accession NM_003254.

DEFINITIONS

Figure 3:
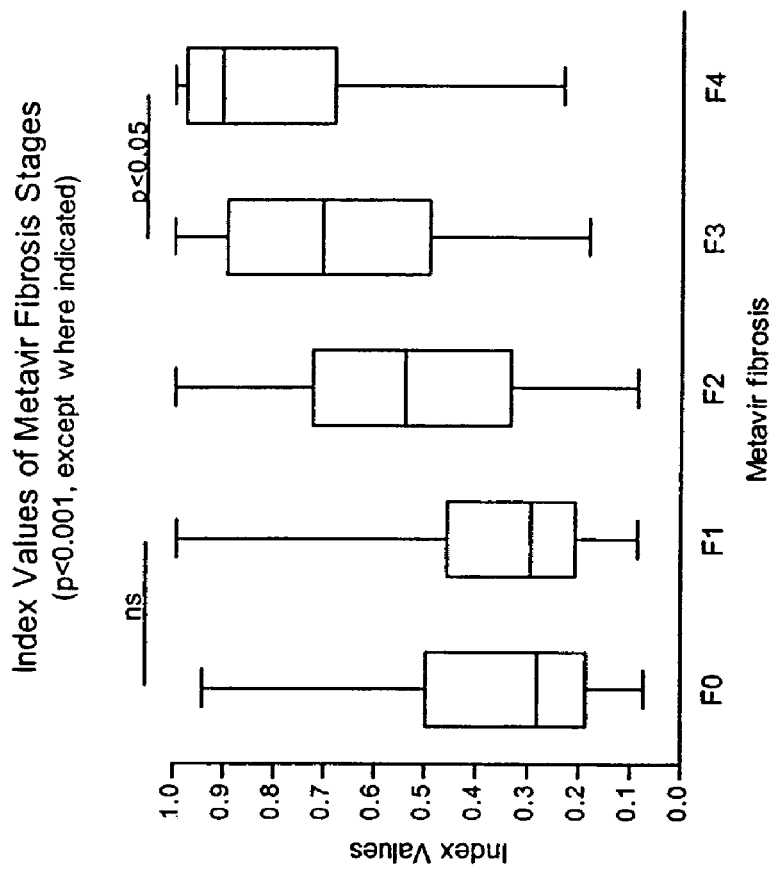
FIG. 3 provides a graph showing the results of the three marker algorithm analysis.

"Tissue fibrosis" as used herein refers to a variety of fibrotic disorders, including but not limited to liver fibrosis, pulmonary fibrosis, kidney fibrosis, prostate fibrosis and breast fibrosis. The methods of the invention can be applied, without limitation, to diagnosing the presence or severity of pulmonary fibrosis, for example, idiopathic pulmonary fibrosis or emphysema; kidney fibrosis; bladder fibrosis; periureteric fibrosis or retroperitoneal fibrosis; endomyocardial fibrosis, aortic aneurysm disease; rheumatoid diseases such as rheumatoid arthritis or systemic lupus erythematosus; or another fibrotic disorder such as Alzheimer's disease.

"Algorithm" refers to any of a variety of statistical analysis used to determine relationships between variables. In the present invention the variables are levels of markers of fibrosis and the algorithm is used to determine, e.g., the presence or severity of tissue fibrosis. In one embodiment logistical regression is used. Other statistical methods, e.g., linear regression, are know to those of skill in the art and also include artificial neural networks (ANN), neuro fuzzy networks (NFN), multilayer perceptron (MLP), learning vector quantization (LVQ) (Freeman et al. In "Neural Networks: Algorithms, Applications and Programming Techniques by Addison-Wesley Publishing Company" 1991, Zadeh Information and Control 1965; 8:338-353, Zadeh "IEEE Trans. on Systems, Man and Cybernetics" 1973; 3:28-44, Gersho et al. In "Vector Quantization and Signal Compression by Kluywer Academic Publishers, Boston, Dordrecht, London" 1992, Hassoun "Fundamentals of Artificial Neural Networks by The MIT Press, Cambridge, Mass., London" 1995). Any number of markers of fibrosis can be analyzed using analgorithm according to the methods of the present invention. For example, levels of up to 2, 3, 4, 5, 6, 7, 8, 9, 10, 15, 20, 25, 30, 35, 40, or 50 markers of fibrosis can be included in an algorithm. In a preferred embodiment levels of three fibrotic markers, α2-MG or A2M, HA, TIMP-1 are determined and analyzed using logistical regression to diagnose a fibrotic disease, using e.g., an index value. In another preferred embodiment, the algorithm is the following $$Index = \frac{Exp^{[-4.3633+(0.0108*HA\,ng/ml)+(0.0015*TIMP-1\,ng/ml)+(0.5357*A2M\,mg/ml)]}}{1 + Exp^{[-4.3633+(0.0108*HA\,ng/ml)+(0.0015*TIMP-1\,ng/ml)+(0.5357*A2M\,mg/ml)]}}$$

and is used to analyze data and provide diagnosis of the presence or severity of liver fibrosis.

"Index value" as used herein refers to a number for an individual patient that is determined using an algorithm for providing diagnosis of the presence or severity of tissue fibrosis. In a preferred embodiment, diagnosis is provided for the presence or severity of liver fibrosis. In another preferred embodiment, the index value will be determined using logistical regression and will be a number between 0 and 1. Such an algorithm would have the following formula:

Index Value=Exp($b0+b1*x1+...+bn*xn$)/(1+Exp
($b0+b1*x1+...+bn*xn$)), wherein
b0 is an intercept value;
b1 is the regression coefficient of the first marker;
x1 is the concentration level of the first marker;
bn is the regression coefficient of the nth marker; and
xn is the concentration level of the nth marker.

A specific preferred example of an algorithm for determining an index value is provided above.

"Index cutoff value" as used herein refers to a number chosen on the basis of population analysis that is used for comparison to an index value of an individual and for diagnosis of the presence or severity of tissue fibrosis. Thus, the index cutoff value is based on analysis of index values determined using an algorithm. Those of skill will recognize that a index cutoff value can be determined according to the needs of the user and characteristics of the analyzed population. When the algorithm is logistical regression the index cutoff value will, of necessity by between 0 and 1. Ranges for index cutoff values include e.g., 0.3 to 0.7 and 0.4 to 0.6. Once an index cutoff value is determined, it is compared to an index value for an individual. Optimal results will be derived from maximization of the balance of sensitivity with specificity. Once an index cutoff value is determined, it is compared to an index value for an individual. A disease state can be indicated by an index value above or below the index cutoff value.

In a preferred embodiment, the algorithm used is listed above and the index cutoff value is 0.42. In this embodiment, individuals with an index value above 0.42 are diagnosed having moderate/severe liver fibrosis, e.g., Metavir scores of F2-F4. Individuals with an index value below 0.42 are diagnosed having no/mild liver fibrosis e.g., Metavir scores of F0-F1.

In another preferred embodiment, the algorithm listed above is used to detect or diagnose liver fibrosis in an individual with NASH. In this embodiment, individuals with an index value above 0.475 are diagnosed having moderate/severe liver fibrosis, e.g., Metavir scores of F3-F4. Individuals with an index value below 0.475 are diagnosed having no/mild or moderate liver fibrosis e.g., Metavir scores of F0-F2.

"Iterative approach" as used herein refers to analysis of fibrotic markers from an individual using more than one algorithm or index cutoff value. For example, two or more algorithms could be used to analyze fibrotic markers with different sets of fibrotic markers being analyzed each algorithm. As another example, a single algorithm could be used to analyze fibrotic markers, but more than one index cutoff value based on the algorithm could be used for diagnosis.

As used herein, the term "indeterminate status" means that an individual cannot be confidently diagnosed with sufficient predictive value. That is the individual cannot be determined to have an F0-F1 (no/mild) or F2-F4 (moderate/severe) fibrosis status. In another embodiment, the individual cannot be determined to have an F0-F2 (no/mild or moderate) or F3-F4 (moderate/severe) fibrosis status.

"Marker of fibrosis" as used herein refers to any biochemical, serological markers or any other clinical or echographic characteristics, that can be correlated with the presence of fibrotic disease. Examples of biochemical and serological markers include, yet are not limited to, α2-MG or A2M, HA, TIMP-1, PIIINP; laminin; tenascin; collagen type IV; collagen type VI; YKL-40, MMP-3; MMP-2; MMP-9/TIMP-1 complex; sFas ligand; TGF-β1; IL-10; apoA1; apoA2; apoB; integrin 1β; TNF-alpha; MCP-1; leptin; VEGF; PDGF; collagen type I; collagen type XIV; fibronectin; prolyl hydroxylase; nitrotyrosine; nitic oxide; MDA, 4HNE, or LPO; F2-isoprostanes, 8-epi-PGF-2alpha; β-hydroxybutyrate; IGF-1; IGFBP3; and liver FABP. Additional biochemical and serological markers useful in the invention include, without limitation, fibronectin, pseudocholinesterase, manganese superoxide dismutase, N-acetyl-β-glucosaminidase (β-NAG), glutathione peroxidase, connective tissue growth factor (CTGF); platelet derived growth factor (PDGF), PDGF receptor, inducible nitric oxide synthetase, nitrotyrosine, bilirubin, ferritin and α-fetoprotein, γ-glutamyl transpeptidase (GGT), aspartate aminotransferase (AST), alanine aminotransferase (ALT), AST/ALT ratio, albumin, γ-globulins, βγ-block, prothrombin index, Child-Pugh score, PGA index (prothrombin time, GGT concentration and apoA1 concentration), PGAA index (PGA score with α2-macroglobulin level), hemoglobin, mean corpuscular volume, lymphocyte count, cholesterol, urea, creatinine, sodium and platelet count. Assays of detection for the above listed markers of fibrosis are commercially available.

"Differentiate no/mild from moderate/severe" or "diagnose the presence or severity of tissue fibrosis" as used herein refer to methods to diagnose the presence of a fibrotic disease or the absence of a fibrotic disease. They also refer to methods to differentiate different individual stages of fibrotic disease from each other. Liver fibrotic disease is used as a non-limiting example. The severity of liver fibrosis is assessed using a number of well established methods known to those of skill in the art, for example, Ishak, Scheur, Knodell, Ludwig and Batts, and Metavir. Each system using a stage or grade to refer to a severity of liver fibrosis. In one embodiment, the methods of the invention are used to differentiate between no/mild and moderate/severe liver fibrosis based on the Metavir staging system. Metavir has five stages. F0 and F1 refer to no or mild disease and F2, F3, and F4 refer to moderate through severe disease. In another embodiment, cut-off index values are determined for 2 or more Metavir stages. For example, cut-off index values are determined for F0, F1, disease and F2, F3, and F4 disease; or for F0, F1, and F2 disease and F3 and F4 disease, or to some subset comprising two or more Metavir stages. Index cutoff values can also be determined for each individual Matavir stage, i.e., F0 disease, F1 disease, F2 disease, F3 disease, and F4 disease "Monitoring the progression of tissue fibrosis" refers to use of the algorithms of the invention to determine the disease state of an individual. In one embodiment, the index value of the patient is compared to an index value for the same patient that was determined at an earlier time. The method can also be used to predict the progression of a disease. For example, patients hepatitis C progress can progress slowly or rapidly. The methods of the invention can be used to analyze markers of fibrosis and determine a likelihood for a patient to progress either rapidly or slowly, based on the levels of markers of fibrosis in a biological sample.

"Monitoring response to a therapeutic agent" refers to use of the present invention to determine the disease state of an individual after a therapeutic agent has been administered. In one embodiment, the index value of the patient is compared to an index value for the same patient that was determined before initiation of use of the therapeutic agent. A therapeutic agent is any compound, drug or procedure used to improve the health of a patient.

"Anti-fibrotic agent" refers to agent that inhibit fibrosis. Anti-fibrotic agents are known to those of skill in the art and include, but are not limited to cytokines such as interferon and hepatocyte growth factor.

"Anti-viral agent" refer to agents that inhibit viral proliferation and are known to those of skill in the art. In a preferred embodiment anti-viral agents are used against, e.g., hepatitis A virus, hepatitis B virus, hepatitis C virus, and HIV-1 virus.

DETAILED DESCRIPTION OF THE INVENTION

As disclosed herein, the serum levels of a number of biochemical markers were analyzed in a patient population with confirmed hepatitis C and having a known Metavir stage (fibrosis score) of F0 to F4, where F0 represents very low or no fibrosis; F1, F2 and F3 represent intermediate fibrosis stages; and F4 represents severe fibrosis (Knodell et al., *Hepatology* 1:431-435 (1981)).

Based on these findings, the present invention provides a method of diagnosing the presence or severity of liver fibrosis in an individual by detecting α2-MG in a sample from an individual; detecting HA in a sample from the individual; detecting TIMP-1 in a sample from the individual; and diagnosing the presence or severity of liver fibrosis in the individual based on the presence or levels of α2-MG, HA and TIMP-1. In preferred embodiments, the α2-MG, HA and TIMP-1 levels are analyzed using an algorithm (or algorithms) that does not contain indeterminate values. A method of the invention can be useful, for example, for differentiating no or mild (F0-F1) liver fibrosis from moderate to severe (F2-F4) liver fibrosis. Methods of the invention can also be used to differentiate no or mild/moderate (F0-F2) liver fibrosis from moderate to severe (F3-F4) liver fibrosis.

In a preferred embodiment, levels of α2-MG are determined and analyzed in combination with levels of HA and TIMP-1 using an algorithm. Addition of the α2-MG determination to the HA and TIMP-1 analysis can increased the specificity of the algorithm. See, e.g., Examples 3 and 4, herein.

In another embodiment, the methods of the invention (e.g., analysis of α2-MG, HA and TIMP-1 using an algorithm) can be used to diagnose the presence or severity of liver fibrosis in a patient with primary biliary cirrhosis. The methods of the invention can also be used to predict a clinical outcome in a patient with primary biliary cirrhosis. See, e.g., Example 5, herein.

In still another embodiment, the methods of the invention (e.g., analysis of α2-MG, HA and TIMP-1 using an algorithm) can be used to diagnose the presence or severity of liver fibrosis in a patient with NASH. See, e.g., Example 6, herein.

Liver and Other Fibrotic Disorders

The methods of the invention can be useful for diagnosing the presence or severity of liver fibrosis in a variety of individuals including those at risk for, or having one or more symptoms of, a liver disorder characterized by fibrosis. The methods of the invention can be used to diagnose liver fibrosis in an individual having, for example, viral hepatitis such as hepatitis A, B or C virus or a human immunodeficiency virus (HIV) such as HIV-1; chronic persistent hepatitis or chronic active hepatitis; autoimmune liver disease such as autoimmune hepatitis; alcoholic liver disease; fatty liver disease, including nonalcoholic steatohepatitis (NASH); primary biliary cirrhosis; primary sclerosing cholangitis, biliary atresia; liver disease resulting from medical treatment (drug-induced liver disease); or a congenital liver disease. The methods of the invention can be extremely useful, for example, in alleviating concerns of potential liver damage due to methotrexate treatment. Periodic monitoring of liver fibrosis in individuals treated with methotrexate or other drugs associated with risk of liver damage can be conveniently performed using the non-invasive methods of the invention, without the risks associated with liver biopsy.

In one embodiment, the methods of the invention are useful for differentiating individuals having a Metavir score of F0 or F1 from individuals having a Metavir score of F2, F3 or F4. Metavir scoring is a well accepted system for grading liver biopsy specimens and is described in Knodell, supra, 1981. F0 is equivalent to the absence of fibrosis; F1 signifies portal fibrosis without septa. F2 signifies portal fibrosis with a few septa. F3 signifies numerous septa without cirrhosis. F4 signifies cirrhosis.

It is understood that the methods of the invention are useful for diagnosing the presence or severity of fibrosis associated with a variety of fibrotic disorders, including but not limited to liver fibrosis, pulmonary fibrosis, kidney fibrosis, prostate fibrosis and breast fibrosis. The methods of the invention can be applied, without limitation, to diagnosing the presence or severity of pulmonary fibrosis, for example, idiopathic pulmonary fibrosis or emphysema; kidney fibrosis; bladder fibrosis; periureteric fibrosis or retroperitoneal fibrosis; endomyocardial fibrosis, aortic aneurysm disease; rheumatoid diseases such as rheumatoid arthritis or systemic lupus erythematosus; or another fibrotic disorder such as Alzheimer's disease. It is understood that a α2-MG/HA/TIMP-1, alone or in combination with other markers disclosed herein as useful for diagnosing the presence or severity of liver fibrosis also can be used to diagnose the presence or severity of fibrosis in another disorder.

It is understood that the diagnostic methods of the invention are applicable to a variety of individuals including individuals with chronic or active disease, individuals with one or more symptoms of fibrotic disease, asymptomatic or healthy individuals and individuals at risk for one or more fibrotic diseases. It further is clear to the skilled person that the methods of the invention can be useful, for example, to corroborate an initial diagnosis of disease or to gauge the progression of fibrosis in an individual with a previous definitive diagnosis of fibrotic disease. The methods of the invention can be used to monitor the status of fibrotic disease over a period of time and further can be used, if desired, to monitor the efficacy of therapeutic treatment. If desired, the results obtained from a sample from an individual undergoing therapy can be compared, for example, to the individual's baseline results prior to treatment, to results earlier during treatment, or to a historic or reference value.

Samples

A variety of samples can be useful in practicing the methods of the invention including, for example, blood, serum, plasma, urine, saliva and liver tissue. In one embodiment, a single sample is obtained from the individual-to be diagnosed. Such a sample can be, for example, a serum sample.

As used herein, the term "sample" means a biological specimen that contains one or more fibrotic markers such as α2-MG, HA or TIMP-1. A sample can be, for example, a fluid sample such as whole blood, plasma, saliva, urine, synovial fluid or other bodily fluid, or a tissue sample such as a lung, liver, kidney, prostate or breast tissue sample. One skilled in the art understands that fluid samples can be diluted, if desired, prior to analysis.

One skilled in the art understands that a single sample can be obtained from the individual to be diagnosed and can be subdivided prior to detecting α2-MG-, HA- and TIMP-1. One skilled in the art also understands that, if desired, two or more samples can be obtained from the individual to be diagnosed and that the samples can be of the same or a different type. In one embodiment, α2-MG-, HA- and TIMP-1 each are detected in serum samples. In another embodiment, a single serum sample is obtained from an individual and subdivided prior to detecting α2-MG-, HA- and TIMP-1.

α2-macroglobulin

The methods of the invention rely, in part, on detecting α2-macroglobulin in a sample. α2-MG (also referred to herein as A2M) is a conserved, highly abundant component of plasma that functions as a broad spectrum protease-binding protein to clear active proteases from tissue fluids. Unlike active site protease inhibitors, members of the α2-macroglobulin family do not inactivate the catalytic activity of their protease substrates but act by physical entrapment of the target protease within the folds of the α2-MG family member. α2-MG is itself cleaved by target proteases; reorganization of the α2-MG molecule results in sequestering of the target protease within an internal pocket of the α2-MG molecule (Starkey et al., Biochem. J. 131:823-831 (1973)). While an α2-MG entrapped protease is sterically prevented from interacting with macromolecular substrates such as proteins, it remains active against low molecular mass substrates, such as amide and ester compounds, able to diffuse into the α2-MG cage to access the enzymatic site. Thus, α2-MG activity is characterized, in part, by the ability to inhibit proteolytic activity but not amidolytic activity of a protease substrate. α2-MG also is characterized by the ability to shield entrapped proteases from antibodies and high molecular mass active site inhibitors. For example, trypsin bound by α2-MG is protected from inhibition by soybean trypsin inhibitor (STI).

In contrast to the restricted specificity of active-site protease inhibitors, α2-MG acts on a broad spectrum of proteases with diverse substrate specificity and catalytic activity. Such target proteases include trypsin, subtilisin, chymotrypsin, plasmin, elastase, thermolysin and papain. Substrate diversity is determined, in part, by the α2-MG "bait" region, a highly flexible and solvent-exposed sequence of 30-40 residues that contains at least one site sensitive to cleavage by each of the major classes of proteolytic enzyme.

As used herein, the term "α2-macroglobulin" is synonymous with "α2-MG" and means a protein with significant structural homology to human α2-MG (SEQ ID NO: 2) and having broad spectrum protease inhibitory activity. α2-MG contains a unique thiol ester bond that is inactivated by small primary amines such as methylamine. Thus, α2-MG activity can be characterized, in part, by methylamine-sensitive protease inhibitory activity. α2-MG can be distinguished, if desired, from other members of the α2-macroglobulin family such as related protease-binding proteins and C3, C4 and C5 of the complement system (Sottrup-Jensen, "α2-Macroglobulin and Related Thiol Ester Plasma Proteins," in Putnam (Ed.), The Plasma Proteins: Structure, Function and Genetic Control Second edition, Orlando: Academic Press (1987), pages 191-291. It is understood that an assay for detecting α2-MG can be specific for α2-MG or can additionally detect one or more other members of the α2-macroglobulin family.

The methods of the invention rely, in part, on detecting α2-macroglobulin in a sample. As used herein, the phrase "detecting α2-MG" means any quantitative or qualitative assay for determining the presence of α2-MG. As used herein, the phrase "determining the level of α2-MG" means any direct or indirect quantitative assay for α2-MG.

Similarly, detecting any specified fibrotic marker in a sample means determining whether the marker is present in the sample, said fibrotic marker having a positive or negative correlation with liver fibrosis or with another fibrotic disorder such as are described herein above. It is understood that detection can refer to non-quantitative analysis, for example, the presence or absence of a particular trait, variable or biochemical or serological substance.

Diagnosis is based on analyzing the sample for the presence or level of the fibrotic marker or other characteristic and comparing it to a reference value, where the reference value serves to assist in differentiating those with a fibrotic disorder from other individuals. Where the fibrotic marker is a biochemical or serological marker, determining a "level" in a sample means quantifying the fibrotic marker by determining, for example, the relative or absolute amount of RNA, protein or activity of the fibrotic marker. Thus, determining a level in a sample encompasses, without limitation, analysis of relative and absolute RNA, protein and activity levels as well as other direct and indirect measurements of the fibrotic marker as discussed further below. It is understood that any assay useful for determining a "level" of a fibrotic marker also is useful for "detecting" the marker.

A variety of assays for detecting α2-MG are known in the art and include direct and indirect assays for α2-MG RNA, α2-MG protein and α2-MG activity. α2-MG can be detected, or an α2-MG level can be determined, for example, by analysis of α2-MG mRNA levels using routine techniques such as Northern analysis or RT-PCR, or other methods based on hybridization to a nucleic acid sequence that is complementary to a portion of the α2-MG coding sequence. For example, conditions and probes for Northern analysis and RNA slot blot hybridization of α2-MG RNA in human samples are described in Ortego et al., Exp. Eye Res. 65:289-299 (1997), and Simon et al., Cancer Res. 56:3112-3117 (1996), respectively.

α2-MG also can be detected, or an α2-MG level can be determined, by assaying for α2-MG protein by a variety of methods. Immunoassays, including radioimmunoassays, enzyme-linked immunoassays and two-antibody sandwich assays as described further below, are useful in the methods of the invention. For example, in nephelometry assays, complexes of α2-MG and anti-α2-MG antibody result in increased light scatter that is converted to a peak rate signal, which is a function of the sample α2-MG concentration. α2-MG also can be detected, for example, by laser immunonephelometry using a Behring Nephelometer Analyzer (Fink et al., J. Clin. Chem. Clin. Biol. Chem. 27:261-276 (1989)) and rabbit anti-human α2-MG antiserum as described in Naveau et al., Dig. Diseases Sci. 39:2426-2432 (1994), or using the nephelometry assay commercially available from Beckman Coulter (Brea, Calif.; kit #449430). Furthermore, monoclonal and polyclonal anti-α2-MG antibodies useful in immunoassays can be readily obtained from a variety of sources. As examples, affinity purified goat anti-human α2-MG and peroxidase-labeled goat anti-human α2-MG antibodies suitable for immunoassays such as ELISA assays and western blotting are available from Cedarlane Laboratories Limited (Ontario, Canada; CL20010AP and CL20010APHP) and Affinity Biologicals Incorporated (Ontario, Canada; GAA2M-AP and GAA2M-APHRP). Levels of α2-MG protein also can be determined by quantifying the amount of purified α2-MG protein. Purification of α2-macroglobulin can be achieved, for example, by HPLC, alone or in combination with mass spectrophotometry, or as described, for example, in Hall and Roberts, *Biochem. J* 171: 27-38 (1978) or Imber and Pezzo, *J. Biol. Chem.* 256:8134-8139 (1981)). Quantitation can be determined by well known methods including Bradford assays, Coomassie blue staining and assays for radiolabeled protein.

A variety of assays for α2-MG activity also can be useful for detecting α2-MG or determining a level of α2-MG in a sample according to a method of the invention. α2-MG can be detected or a level of α2-MG can be determined indirectly, for example, as a function of inhibition of target protease activity, without a corresponding inhibition of amidolytic activity. As discussed above, α2-MG-bound proteases retain the ability to hydrolyze amide and ester bonds of small substrates, even while high molecular mass substrates such as proteins cannot be hydrolyzed (see, for example, Armstrong et al., *Develop. Compar. Immunol.* 23:375-390 (1999)). As an example, α2-MG can be detected or the level of α2-MG can be determined by assaying for inhibition of trypsin, subtilisin, chymotrypsin, plasmin, elastase, thermolysin, or papain activity without inhibition of amidolytic activity. Convenient substrates to be analyzed include $^{14}C$-labeled casein and $^{125}I$-fibrin.

The characteristic of broad protease substrate specificity distinguishes α2-MG from inhibitors of protease active sites. Based on this characteristic, α2-MG can be detected or the level of α2-MG can be determined by assaying for inhibition of the activity of two or more proteases with different active site specificities. α2-MG can be detected or the level of α2-MG in a sample can be determined, for example, by analyzing the reduction in protease activity of two or more target proteases such as two or more of the following proteases: trypsin, subtilisin, chymotrypsin, plasmin, elastase, thermolysin and papain. Labeled protease substrates such as $^{14}C$-casein or $^{125}I$-fibrin can be useful in such methods (Armstrong et al., supra, 1999).

α2-MG also can be detected or the level of α2-MG determined based on the ability of α2-MG to shield a bound protease from an antibody or a high molecular weight inhibitor. A target protease such as trypsin, subtilisin, chymotrypsin, plasmin, elastase, thermolysin, or papain can be added to a plasma sample. Following removal of unbound protease, for example, by immunoprecipitation with anti-protease antibody, the amount of protease bound by α2-MG can be determined using a low molecular mass amide or ester substrate. The amount of hydrolyzed low molecular mass substrate is an indicator of the amount of protected, α2-MG-bound, protease and, therefore, of the concentration of α2-MG. Similarly, a sample can be reacted first with a protease such as trypsin and subsequently with excess protease inhibitor such as soybean trypsin inhibitor before assaying residual trypsin activity with a low molecular mass substrate, such as the amide BApNA ($N^\alpha$-benzoyl-DL-arginine p-nitroanilide (Ganrot, *Clin. Chem. Acta* 14:493-501 (1966); Armstrong et al., *J. Exp. Zool.* 236:1-9 (1985)). Trypsin not sequestered by α2-MG is inactivated by the trypsin inhibitor, with only α2-MG-protected trypsin remaining capable of substrate hydrolysis. Thus, a positive reaction in a soybean trypsin inhibitor assay detects α2-MG and is a quantitative measure of the amount of α2-MG (Armstrong et al., supra, 1999). One skilled in the art understands that the presence of low molecular mass protease inhibitors capable of inactivating α2-MG-bound enzyme can affect the results obtained with such an assay. It is further understood that these and other routine assays for α2-MG activity, as well as α2-MG RNA or protein levels, can be useful for detecting α2-MG or determining a level of α2-MG in a method of the invention.

Hyaluronic Acid

The methods of the invention further rely, in part, on detecting hyaluronic acid or determining a level of hyaluronic acid in a sample. Hyaluronic acid, also known as hyaluronate or hyaluronan, is a high molecular weight polysaccharide with an unbranched backbone made up of alternating glucuronic acid and β(1,3)-N-acetylglucosamine moieties linked by β-1,4 linkages. Hyaluronic acid can have a length of a few to more than 1,000 dimeric units, with each dimeric unit having a molecular weight of about 450 D. Hyaluronic acid, which is produced principally by fibroblasts and other specialized connective tissue cells, plays a structural role in the connective tissue matrix. Furthermore, hyaluronic acid is widely distributed throughout the body and can be found as a free molecule in, for example, plasma, synovial fluid and urine. In plasma, hyaluronic acid has a relatively short half-life.

Serum HA levels can be elevated in liver diseases including cirrhosis (Bramley et al., *J. Hepatol.* 13:8-13 (1991); Ueno et al., *Gastroenterol.* 105:475-481 (1993); Oberti et al., *Gastroenterol.* 113:1609-1616 (1997); and McHutchison et al., *J. Gastroenterol. Hepatol.* 15:945-951 (2000)). Serum HA levels also can be elevated during synovial inflammation and cartilage destruction seen in rheumatoid arthritis; these levels have been found to correlate with disease activity and degree of synovial involvement (Konttinen et al., *Clin. Chimica Acta* 193:39-48 (1990); Poole et al., *Arthritis Rheum.* 37:1030-1038 (1994); Goldberg et al., *Arthritis Rheum.* 34: 799-807 (1991); and Emlem et al., *J. Rheum.* 23:974-978 (1996)). Elevated serum levels of HA also can be present, for example, in patients with osteoarthritis (OA), progressive systemic sclerosis (PSS) and systemic lupus erythematosus (SLE).

As used herein, the term "hyaluronic acid" is synonymous with "HA" and means a polymer of two or more dimeric units of alternating glucuronic acid and β(1,3)-N -acetylglucosamine moieties linked by β-1,4 linkages. As used herein, the phrase "detecting HA" means any quantitative or qualitative assay for determining the presence of HA, and the phrase "determining the level of HA" means any direct or indirect quantitative assay for HA. In view of the above, it is understood that the phrase "detecting HA" encompasses "determining the level of HA."

HA can be detected or a level of HA can be determined using one of a variety of well known assays based on HA-binding proteins or anti-HA antibodies, or by quantitation of purified HA. HA-binding proteins, for example, can be useful in detecting HA; a radiometric assay for HA based on $^{125}I$-labelled HA-binding protein is available from Pharmacia (Guechot et al., *Clin. Chem.* 42:558-563 (1996). Other commercial assays based on HA-binding proteins are available, for example, from Corgenix (Westminster, Conn.; kit 029001). In addition, HA can be detected or a level of HA can be determined using hyaluronectin as described in Maingonnat and Delpech, *Ann. Clin. Biochem.* 28:305-306 (1991), or using the kit available from Nalgenunc International (Rochester, N.Y.; Delpech and Bertrand, *Anal. Biochem.* 149:555-565 (1985)). Assays for detecting HA or determining a level of HA include a variety of competitive and non-competitive binding assays, for example, competitive binding assays using $^{125}$I-labeled HA binding protein; competitive binding assays based on alkaline phosphatase labeled-hyaluronectin (HN); and non-competitive binding assays based on peroxidase-labeled proteoglycan or peroxidase-labeled HA-binding protein, among others (Lindquist et al., *Clin. Chem.* 38:127-132 (1992)). See, also, Delpech and Bertrand, supra, 1985; Engstrom-Laurent et al., *Scand. J. Clin. Lab. Invest.* 45:497-504 (1985); Brandt et al., *Acta Otolaryn.* 442 (Suppl.):31-35 (1987); Goldberg, *Anal. Biochem.* 174:448-458 (1988); Chichibu et al., *Clin. Chim. Acta* 181:317-324 (1989); Li et al., *Conn. Tissue Res.* 19:243-254 (1989); Poole et al., *Arth. Rheum.* 33:790-799 (1990); Poole et al., *J. Biol. Chem.* 260:6020-6025 (1985); and Laurent and Tengblad, *Anal. Biochem.* 109:386-394 (1980)). Assays for detecting HA or determining a level of HA in a sample can be performed using a variety of immunoassay formats, including radioimmunoassays and enzyme-linked immunoassays. Anti-HA antiserum useful in immunoassays can be, for example, affinity purified sheep anti-HA antiserum available from Biotrend (Cologne, Germany; #5029-9990).

A level of HA also can be determined by purifying HA from a sample, and quantifying the amount of purified polysaccharide. High performance liquid chromatography can be used alone or in conjunction with mass spectrophotometry. As an example, HPLC can be used to determine HA levels after digestion of samples containing an internal standard with hyaluronidase, separation by a reversed phase octadecylsilyl column and elution with 0.01 M tetrabutylammonium phosphate-acetonitrile (83:17, v/v) at pH 7.35 (Payan et al., *J. Chromatogr.* 566:9-18 (1991)).

HA levels have been shown to correlate with hyaluronidase levels (Bray et al., *Am. Rev. Respir. Dis.* 3:284-288 (1991)). Thus, HA can be detected or a level of HA can be determined indirectly by assaying for hyaluronidase activity. Assays for hyaluronidase activity are known in the art, as described in Bray et al., supra, 1991. One skilled in the art understands that these and other routine assays for determining hyaluonidase or HA levels are encompassed by the phrases "detecting HA" and "determining the level of HA" and can be useful in diagnosing the presence or severity of liver fibrosis according to a method of the invention.

TIMP-1

The methods of the invention also are based on detecting TIMP-1 in a sample and, in particular embodiments, on determining a level of TIMP-1 in a sample. Tissue inhibitors of metalloproteinases (TIMPs) regulate the activity of the matrix metalloproteinases (MMPs), which are an important group of ECM-degradative enzymes that include gelatinase A (MMP-2) and gelatinase B (MMP-9). In normal liver, matrix components such as collagens, fibronectin, laminin, tenascin, undulin and entactin are constantly remodeled by matrix degrading enzymes to control deposition of extracellular matrix. Elevation of TIMP levels results in inhibition of MMP activity and favors the accumulation of extracellular matrix. The TIMPs, which include TIMP-1, TIMP-2, TIMP-3 and TIMP-4, interact with the matrix metalloproteinases with a 1:1 stoichiometry and inhibit metalloprotease activity through reversible non-covalent binding. TIMP-1, TIMP-2 and TIMP-3 have similar MMP-inhibitory activities, inhibiting the proteolytic activity of collagenase, gelatinase, stromelysin, proteoglycanase and metalloelastases although their localization and regulation differ (Cawston et al., "Protein Inhibitors of Metalloproteinases" in Barrett and Salvesen (Eds), Proteinase Inhibitors Amsterdam Elsevier pages 589-610 (1986)).

Human TIMP-1 is a 184 amino acid sialoglycoprotein with a molecular weight of 28.5 kDa (Murphy et al., *Biochem. J.* 195:167-170 (1981); Dockerty et al., *Nature* 318:66-69 (1985); and Bodden et al., *J. Biol. Chem.* 269:18943-18952 (1994)). TIMP-1 inhibits all active metalloproteinases, for example, interstitial collagenase MMP-1 as well as stromelysin and gelatinase B (MMP-9). The nucleic acid sequence (SEQ ID NO: 3) and corresponding amino acid sequence (SEQ ID NO: 4) of human TIMP-1 are shown in FIG. 2.

As used herein, the term "tissue inhibitor of metalloproteinase-1" is synonymous with "TIMP-1" and means a protein with significant structural homology to human TIMP-1 (SEQ ID NO: 4) that inhibits the proteolytic activity of metalloproteinases with a specificity similar to human TIMP-1. The presence of human TIMP-1 can be conveniently detected by the presence of epitopes reactive with a known specific anti-TIMP-1 antibody such as 7-6C1 or 7-23G9.

As used herein, the phrase "detecting TIMP-1" means any quantitative or qualitative assay for determining the presence of TIMP-1, and the phrase "determining the level of TIMP-1" means any direct or indirect quantitative assay for TIMP- 1. In view of the above, it is understood that the phrase "detecting TIMP-1" encompasses "determining the level of TIMP-1."

Assays for detecting TIMP-1 and for determining a level of TIMP-1 include well known assays for TIMP-1 RNA, protein and enzymatic activity. Methods of determining TIMP-1 RNA levels by Northern analysis or RT-PCR are well known in the art (Yoshiji et al., *Int. J. Cancer* 69:131-134 (1996); Janowska-Wieczorek et al., *Exp. Hematol.* 28:1274-1285 (2000); and Groft et al., *Br. J. Cancer* 85:55-63 (2001)) as described further below. TIMP-1 protein can be detected or the level of TIMP-1 protein can be conveniently determined, for example, by radioimmunoassay as described in Brophy et al., *Biochem. Biophys. Res. Comm.* 167:898-903 (1990) or by two-antibody sandwich assay as described in Murawaki et al., *Clinica Chimica Acta* 218:47-58 (1993). Plasma concentrations of TIMP-1 protein can be assayed by ELISA with a kit commercially available from Amersham Pharmacia (see, also Example III). Levels of TIMP-1 protein also can be determined by quantifying the amount of purified TIMP-1 protein. Purification of TIMP- 1 can be achieved, for example, by HPLC, alone or in combination with mass spectrophotometry, or as described, for example, in Murphy et al., *Biochem. J.* 195:167-170 (1981), or Stricklin and Welgus, *J. Biol. Chem.* 258:12252-12258 (1983). TIMP-1 also can be detected or a level of TIMP-1 determined by assaying for inhibition of the activity of one or more metalloproteases, for example, using reverse gelatin zymography as described in Kossakowska et al., *Amer. J. Pathology* 153:1895-1902 (1998). Assays for TIMP-1 RNA, protein or activity are described further hereinbelow, and one skilled in the art understands that these and other routine assays for detecting TIMP-1 are encompassed by the methods of the invention.

Statistical Analysis

As disclosed herein, levels of α2-MG, HA, and TIMP-1 are detected or determined in a sample from a patient and analyzed using an algorithm to detect tissue fibrosis. Other markers of fibrosis can also be detected or determined in a sample from a patient and analyzed in combination with the α2-MG, HA, and TIMP-1 levels using an algorithm to detect tissue fibrosis. In a preferred embodiment, a diagnosis of liver fibrosis is made. Other methods of diagnosing liver fibrosis are disclosed in WO 03/073822, which is herein incorporated by reference for all purposes.

An algorithm is any of a variety of statistical analysis used to determine relationships between variables. In the present invention the variables are levels of markers of fibrosis and the algorithm is used to determine, e.g., the presence or severity of tissue fibrosis. In one embodiment logistical regression is used. Other statistical methods, e.g., linear regression, are know to those of skill in the art and also include artificial neural networks (ANN), neuro fuzzy networks (NFN), multilayer perceptron (MLP), learning vector quantization (LVQ) (Freeman et al. In "Neural Networks: Algorithms, Applications and Programming Techniques by Addison-Wesley Publishing Company" 1991, Zadeh Information and Control 1965; 8:338-353, Zadeh "IEEE Trans. on Systems, Man and Cybernetics" 1973; 3:28-44, Gersho et al. In "Vector Quantization and Signal Compression by Kluywer Academic Publishers, Boston, Dordrecht, London" 1992, Hassoun "Fundamentals of Artificial Neural Networks by The MIT Press, Cambridge, Mass., London" 1995). Any number of markers of fibrosis can be analyzed using an algorithm according to the methods of the present invention. For example, levels of up to 2, 3, 4, 5, 6, 7, 8, 9, 10, 15, 20, 25, 30, 35, 40, or 50 markers of fibrosis can be included in an algorithm. In a preferred embodiment levels of three fibrotic markers, α2-MG or A2M, HA, and TIMP-1, are determined and analyzed using logistical regression to diagnose a fibrotic disease. In another preferred embodiment, the algorithm is the following $$\text{Index} = \frac{\text{Exp}^{[-4.3633+(0.0108*\text{HA ng/ml})+(0.0015*\text{TIMP-1 ng/ml})+(0.5357*\text{A2M mg/ml})]}}{1+\text{Exp}^{[-4.3633+(0.0108*\text{HA ng/ml})+(0.0015*\text{TIMP-1 ng/ml})+(0.5357*\text{A2M mg/ml})]}}$$

and is used to analyze data and provide diagnosis of the presence or severity of liver fibrosis.

An index value is determined for an individual patient using an algorithm for providing diagnosis of the presence or severity of tissue fibrosis. In a preferred embodiment, diagnosis is provided for the presence or severity of liver fibrosis. In another preferred embodiment, the index value will be determined using logistical regression and will be a number between 0 and 1.

An index cutoff value is a number chosen on the basis of population analysis that is used for comparison to an index value of an individual and for diagnosis of the presence or severity of tissue fibrosis. Thus, the index cutoff value is based on analysis of index values determined for a patient population using an algorithm. Those of skill will recognize that a index cutoff value can be determined according to the needs of the user and characteristics of the analyzed population. When the algorithm is logistical regression the index cutoff value will, of necessity by between 0 and 1. Ranges for index cutoff values include e.g., 0.3 to 0.7 and 0.4 to 0.6. Once an index cutoff value is determined, it is compared to an index value for an individual. A disease state can be indicated by an index value above or below the index cutoff value. In a preferred embodiment, the algorithm used is listed above and the index cutoff value is 0.42. In this embodiment, individuals with an index value above 0.42 are diagnosed having moderate/severe liver fibrosis. Individuals with an index value below 0.42 are diagnosed having no/mild liver fibrosis.

The analysis of marker levels can be done using an iterative approach, that is, an analysis of fibrotic markers from an individual using more than one algorithm or index cutoff value. For example, two or more algorithms could be used to analyze fibrotic markers with different sets of fibrotic markers being analyzed each algorithm. As another example, a single algorithm could be used to analyze fibrotic markers, but more than one index cutoff value based on the algorithm could be used for diagnosis.

The methods of the invention based on an algorithm to analyze the levels of the α2-MG, HA and TIMP-1 markers can be useful in differentiating no or mild liver fibrosis from moderate to severe liver fibrosis in a variety of patient populations. Such methods can be useful, for example, in diagnosing an individual having a liver disease such as viral hepatitis, autoimmune liver disease such as autoimmune hepatitis, alcoholic liver disease, fatty liver disease or drug-induced liver disease. In one embodiment, a method of the invention is used to differentiate no or mild liver fibrosis from moderate to severe liver fibrosis in an individual infected with hepatitis C virus. Samples useful in a method of the invention based on dual cut-off values include, but are not limited to, blood, serum, plasma, urine, saliva and liver tissue. In one embodiment, a method of the invention is practiced by determining the α2-MG level, HA level and TIMP-1 level in one or more serum samples.

One skilled in the art can select an algorithm or index cut off values to achieve one or more clinically useful parameters, such as a desired sensitivity or specificity, or a desired negative predictive value, positive predictive value or accuracy for a patient population having a particular fibrosis prevalence. Receiver operating characteristic curves (ROC) methodology can be used, for example, to select the appropriate cut-off values. In other embodiments, design of experiments (DOE) analysis can be used, but typically DOE is most useful when cutoffs are determined for multiple analytes.

The clinical parameters of sensitivity, specificity, negative predictive value, positive predictive value and accuracy are calculated using true positives, false positives, true negatives and false negatives. A "true positive" sample is a sample positive for the indicated stage of fibrosis according to clinical biopsy, which is also diagnosed positive according to a method of the invention. A "false positive" sample is a sample negative for the indicated stage of fibrosis by biopsy, which is diagnosed positive according to a method of the invention. Similarly, a "false negative" is a sample positive for the indicated stage of fibrosis by biopsy, which is diagnosed negative according to a method of the invention. A "true negative" is a sample negative for the indicated stage of fibrosis by biopsy, and also negative for fibrosis according to a method of the invention. See, for example, Motulsky (Ed.), Intuitive Biostatistics New York: Oxford University Press (1995).

As used herein, the term "sensitivity" means the probability that a diagnostic method of the invention gives a positive result when the sample is positive, for example, fibrotic with a Metavir score of F2-F4. Sensitivity is calculated as the number of true positive results divided by the sum of the true positives and false negatives. Sensitivity essentially is a measure of how well a method correctly identifies those with fibrotic disease.

As used herein, the term "specificity" means the probability that a diagnostic method of the invention gives a negative result when the sample is not positive, for example, not of Metavir fibrosis stage F2-F4. Specificity is calculated as the number of true negative results divided by the sum of the true negatives and false positives. Specificity essentially is a measure of how well a method excludes those who do not have fibrosis.

The term "negative predictive value," as used herein, is synonymous with "NPV" and means the probability that an individual diagnosed as not having fibrosis actually does not have the disease. Negative predictive value can be calculated as the number of true negatives divided by the sum of the true negatives and false negatives. Negative predictive value is determined by the characteristics of the diagnostic method as well as the prevalence of fibrosis in the population analyzed.

The term "positive predictive value," as used herein, is synonymous with "PPV" and means the probability that an individual diagnosed as having fibrosis actually has the condition. Positive predictive value can be calculated as the number of true positives divided by the sum of the true positives and false positives. Positive predictive value is determined by the characteristics of the diagnostic method as well as the prevalence of fibrosis in the population analyzed.

Predictive values, including negative and positive predictive values, are influenced by the prevalence of the disease in the population analyzed.

As used herein, the term "accuracy" means the overall agreement between the diagnostic method and the disease state. Accuracy is calculated as the sum of the true positives and true negatives divided by the total number of sample results and is affected by the prevalence of fibrosis in the population analyzed.

Methods Not Limited to Specific Markers

The present invention also provides a method of diagnosing the presence or severity of tissue fibrosis in an individual by comparing an index value from an individual to an index cut off value based on a population, wherein the index value and the index cut off values are based on an algorithm used to analyze levels of $\alpha$2-MG or A2M, HA, and TIMP-1 in a sample from the individual.

In one embodiment, an index value based on levels of $\alpha$2-MG or A2M, HA, and TIMP-1 is compared to an index cut off value based on those same levels to diagnose tissue fibrosis. In a further embodiment, the levels of $\alpha$2-MG or A2M, HA, and TIMP-1 and at least one, two, three, four or five additional markers of fibrosis are compared to a cut-off value based on those same levels. A method of the invention can be useful, for example, to differentiate no or mild liver fibrosis from moderate to severe liver fibrosis.

Like other methods of the invention, a method of the invention based on comparison of at least $\alpha$2-MG or A2M, HA, and TIMP-1 fibrotic markers can be used to diagnose the presence or severity of liver fibrosis in an individual having or suspected of having any liver disorder, including viral hepatitis, autoimmune liver disease such as autoimmune hepatitis, alcoholic liver disease, fatty liver disease or drug-induced liver disease, or any of the other liver diseases described herein above. Similarly a method of the invention based on comparison of at least $\alpha$2-MG or A2M, HA, and TIMP-1 fibrotic markers can be used to diagnose the presence or severity of fibrotic disorders including pulmonary fibrosis, kidney fibrosis, prostate fibrosis, breast fibrosis or a rheumatoid disease, or another fibrotic disorder described herein or known in the art.

A method of the invention relies on comparison of an index value to a predetermined index cut-off value. For markers that positively correlate with fibrosis, positivity is indicated by a level that is greater than the predetermined cut-off value. For markers that negatively correlate with fibrosis, positivity is indicated by a level that is less than the predetermined cut-off value. Cut-off values useful in the methods of the invention can be determined as described herein, for example, using ROC analysis.

As for the other diagnostic methods of the invention, these methods can be practiced using a variety of fibrotic markers known in the art or described herein. Such fibrotic markers include, without limitation, $\alpha$2-MG, HA, TIMP-1, PIIINP, laminin, tenascin, collagen type IV, collagen type VI, YKL-40, MMP-3, MMP-2, MMP-9/TIMP-1 complex, sFas ligand, TGF-$\beta$1, IL-10, apoA1, apoA2 or ApoB. Additional serological, biochemical, clinical and echographic fibrotic markers are described herein above or are known in the art and can be included in any combination in a method of the invention. For example, the methods of the invention can be used in combination with glycan profiles in a sample from the individual. Glycan profiles are disclosed in WO 03/087833, which is herein incorporated by reference for all purposes. Furthermore, it is understood that comparison of the first and second fibrotic markers and any additional fibrotic markers can be performed simultaneously or in any order and using any combination of assay formats.

As described above, the "level" of a fibrotic marker can be a relative or absolute amount of, for example, RNA, protein or activity and can be a direct or indirect measurement of the fibrotic marker. In addition, the value of the level can be obtained from a secondary source, such as a physician or diagnostic laboratory or can be determined using any convenient sample and assay, including but not limited to those described herein above. Methods useful in determining the level of a fibrotic marker in order to perform the comparisons included in the methods of the invention encompass, for example, hybridization methods such as RT-PCR and RNA blot analysis, immunoassays including enzyme-linked immunosorbent assays (ELISAs) and radioimmunoassays (RIAs), sandwich immunoassays, quantitative western blotting and other standard assays for determining protein levels, and, where applicable, assays for the activity of the fibrotic marker. Such assays are routine in the art and described herein above.

The present invention further provides a method of diagnosing the presence or severity of liver fibrosis in an individual by comparing a level of a first fibrotic marker X in the individual to a cut-off value X1 to determine whether the individual is positive for the first fibrotic marker X; comparing a level of a second fibrotic marker Y in the individual to a cut-off value Y1 to determine whether the individual is positive for the second fibrotic marker Y; comparing a level of a third fibrotic marker Z in the individual to a cut-off value Z1 to determine whether the individual is positive for the third fibrotic marker Z; and diagnosing the presence or severity of liver fibrosis in the individual based on positivity or negativity for X, Y and Z, where the cut-off values X1, Y1 and Z1 are optimized individually to give a desired performance characteristic. In one embodiment, levels of $\alpha$2-MG, HA and TIMP-1 are compared. In other embodiments, the levels of exactly three, at least three, at least four, or at least five fibrotic markers are compared. A method of the invention can be useful, for example, in differentiating no or mild liver fibrosis from moderate to severe liver fibrosis. Index cut-off values can be optimized as described herein, for example, using ROC analysis. In other embodiments, the index cut-off values X1, Y1, X2 and Y2 are optimized individually to give a desired performance characteristic. Such performance characteristics include particular sensitivities, specificities, PPVs, NPVs and accuracies, as described herein above.

"""Methodology

A variety of means can be useful for detecting α2-MG, HA and TIMP-1 and for determining a level of α2-MG, HA and TIMP in a sample. In one embodiment, the invention is practiced by determining the level of α2-MG protein in a sample from the individual to be diagnosed using, for example, one or more α2-MG-specific binding agents such as anti-α2-MG antibodies. In another embodiment, a method of the invention is practiced by assaying for α2-MG activity in a sample from the individual.

A variety of means also can be used in a method of the invention to detect HA or determine a level of HA in a sample. In one embodiment, the invention is practiced by determining the level of HA in a sample using one or more HA-specific binding agents such as HA-binding proteins or anti-HA antibodies.

Similarly, a variety of means can be used in a method of the invention to detect TIMP-1 or determine a level of TIMP-1 in a sample. In one embodiment, the invention is practiced by determining the level of TIMP-1 protein in a sample from the individual to be diagnosed. The level of TIMP-1 protein can be determined, for example, using one or more TIMP-1-specific binding agents such as anti-TIMP-1 antibodies. In another embodiment, the invention is practiced by assaying for TIMP-1 activity in a sample from the individual to be diagnosed.

In a particular embodiment, the invention provides a method of diagnosing the presence or severity of liver fibrosis in an individual by determining the level of α2-MG protein in a sample from the individual; determining the level of HA in a sample from the individual; and determining the level of TIMP-1 protein in a sample from the individual; and diagnosing the presence or severity of liver fibrosis in the individual based on the levels of α2-MG protein, HA and TIMP-1 protein. If desired, the level of α2-MG protein, HA and TIMP-1 protein each can be determined using an enzyme-linked assay.

In a further embodiment, the present invention provides a method of differentiating no or mild liver fibrosis from moderate to severe liver fibrosis in an individual by contacting an appropriate dilution of a sample from the individual with anti-α2-MG antibody under conditions suitable to form a first complex of α2-MG and anti-α2-MG antibody; washing the first complex to remove unbound molecules; determining the amount of α2-MG-containing first complex; contacting an appropriate dilution of a sample from the individual with a HA-binding protein under conditions suitable to form a second complex of HA and HA-binding protein; washing the second complex to remove unbound molecules; determining the amount of HA-containing second complex; contacting an appropriate dilution of a sample from the individual with anti-TIMP-1 antibody under conditions suitable to form a third complex of TIMP-1 and anti-TIMP-1 antibody; washing the third complex to remove unbound molecules; determining the amount of TIMP-1-containing third complex; and differentiating no or mild liver fibrosis from moderate to severe liver fibrosis in the individual based on the amounts of α2-MG, HA and TIMP-1-containing complexes.

It is understood that detecting α2-MG, HA and TIMP-1, as discussed further below, can be accomplished by assaying for the amount of protein or polysaccharide directly, or, in the case of α2-MG and TIMP-1, can be determined by assaying for RNA levels or enzyme activity of a protease regulated by α2-MG or TIMP-1. Similarly, where one or more additional fibrotic markers is detected in a method of the invention, the marker can be assayed directly, or a precursor such as RNA, or a breakdown or proteolytic product, or an activity correlated with levels of the marker can be assayed. It is understood that determining a level of α2-MG, HA, and TIMP-1, or a level of any additional marker of fibrosis, can be performed using absolute values, for example, for RNA or protein levels or enzyme activity, or can be determined as relative values in comparison to one or more reference values.

It further is understood that each of the three fibrotic marker assays (α2-MG/HA/TIMP-1), as well as any additional assays, is performed independently of the others, in any order, and that any combination of assay formats is encompassed by the invention. As an example, a level of α2-MG and HA can be determined by assaying for the concentration of α2-MG and HA while a level of TIMP-1 is determined by assaying for TIMP-1 enzyme activity. As another example, a level of α2-MG can be determined using a radioimmunoassay, while levels of HA and TIMP-1 are determined using enzyme-linked assays. One skilled in the art understands that detection of the three fibrotic markers (α2-MG/HA/TIMP-1 ) and detection of any additional markers can be performed simultaneously or in any order. Furthermore, a single sample such as a serum sample can be obtained from an individual and subdivided into three portions for detecting α2-MG, HA and TIMP-1, or the markers can be detected using different samples, which can be of the same or a different type and can be undiluted or diluted to the same or different extents. Where two or more samples are used, the samples are usually obtained from the individual within a relatively short time frame, for example, several days to several weeks.

RNA Methods

Hybridization methods can be used to detect α2-MG or TIMP-1 mRNA or determine the level of α2-MG or TIMP-1 mRNA or the mRNA of another fibrotic marker useful in the invention. Numerous methods are well known in the art for determining mRNA levels by specific or selective hybridization with a complementary nucleic acid probe. Such methods include solution hybridization procedures as well as solid-phase hybridization procedures in which the probe or sample is immobilized on a solid support. Specific examples of useful methods include amplification methods such as target and signal amplification methods and include PCR (polymerase chain reaction) and reverse-transcriptase-PCR (RT-PCR); transcription mediated amplification (Gen-Probe Incorporated; San Diego, Calif.); branched chain DNA (bDNA) amplification (Bayer Diagnostics; Emeryville, Calif.); strand displacement amplification (SDA; Becton Dickinson; Franklin Lakes, N.J.); and ligase chain reaction (LCR) amplification (Abbott Laboratories; Abbott Park, Ill.). Additional methods useful in the invention include RNase protection; Northern analysis or other RNA blot, dot blot or membrane-based technology; dip stick; pin; and two-dimensional array immobilized onto a chip. Conditions are well known in the art for quantitative determination of mRNA levels using both solution and solid phase hybridization procedures as described, for example, in Ausubel et al., Current Protocols in Molecular Biology (Supplement 47), John Wiley & Sons, New York (1999).

The polymerase chain reaction (PCR) RT-PCR can be useful in the methods of the invention. PCR or RT-PCR can be performed with isolated RNA or crude or partially fractionated samples, for example, cells pelleted from a whole blood sample. PCR methods are well known in the art as described, for example, in Dieffenbach and Dveksler, PCR Primer: A Laboratory Manual, Cold Spring Harbor Press, Plainview, N.Y. (1995). Multisample formats such as two-dimensional arrays offer the advantage of analyzing numerous different samples in a single assay. Solid-phase dip stick-based methods also can be useful in the invention and offer the advantage of being able to rapidly analyze a fluid sample and obtain an immediate result.

Probes for detecting α2-MG and TIMP-1 mRNA or for determining α2-MG and TIMP-1 mRNA levels are well known in the art. One skilled in the art can use, for example, a probe corresponding to some or all of the human α2-MG nucleic acid sequence shown in FIG. 1 (SEQ ID NO: 1) or some or all of the human TIMP-1 nucleic acid sequence shown in FIG. 2 (SEQ ID NO:3), respectively. Appropriate conditions for various assay formats for detecting α2-MG and TIMP-1 mRNA or for determining α2-MG and TIMP-1 mRNA levels are well known in the art or can be established using routine methods. As an example, conditions and probes for Northern analysis of α2-MG RNA in human samples are described, for example, in Ortego et al., supra, 1997. As another example, conditions and probes for RNA slot blot hybridization to determine α2-MG RNA expression in human samples are described in Simon et al., supra, 1996. Similarly, Northern analysis of TIMP-1 RNA in human samples can be performed as described, for example, in Yoshiji et al., supra, 1996; RT-PCR assays for TIMP-1 in human samples also are well known in the art as described, for example, in Janowska-Wieczorek et al., supra, 2000, and Groft et al., supra, 2001. The skilled person understands that these and other assays can be useful for detecting α2-MG or TIMP-1 or for determining α2-MG or TIMP-1 levels, or the levels of other fibrotic markers useful in the methods of the invention.

Immunoassays

A variety of immunoassay formats, including competitive and non-competitive immunoassay formats, antigen capture assays and two-antibody sandwich assays also are useful the methods of the invention (Self and Cook, *Curr. Opin. Biotechnol.* 7:60-65 (1996)). In one embodiment, a method of the invention relies on one or more antigen capture assays. In an antigen capture assay, antibody is bound to a solid phase, and sample is added such that α2-MG, HA, TIMP-1, YKL-40 or another fibrotic marker antigen is bound by the antibody. After unbound proteins are removed by washing, the amount of bound antigen can be quantitated, if desired, using, for example, a radioassay (Harlow and Lane, Antibodies A Laboratory Manual Cold Spring Harbor Laboratory: New York, 1988)). One skilled in the art understands that immunoassays useful in the invention are performed under conditions of antibody excess, or as antigen competitions, to quantitate the amount of antigen and, thus, determine a level of α2-MG, HA, or TIMP-1.

Enzyme-linked immunosorbent assays (ELISAs) can be useful in the methods of the invention. An enzyme such as horseradish peroxidase (HRP), alkaline phosphatase (AP), β-galactosidase or urease can be linked, for example, to an anti-α2-MG, anti-HA, anti-TIMP-1 antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.) as described further below.

Chemiluminescent detection also can be useful for detecting α2-MG, HA, or TIMP-1 or for determining a level of α2-MG, HA, or TIMP-1 or another fibrotic marker according to a method of the invention. Chemiluminescent secondary antibodies can be obtained commercially from various sources such as Amersham.

Fluorescent detection also can be useful for detecting α2-MG, HA, or TIMP-1 or for determining a level of α2-MG, HA, or TIMP-1 or another fibrotic marker in a method of the invention. Useful fluorochromes include, without limitation, DAPI, fluorescein, Hoechst 33258, R-phycocyanin, B-phycoerythrin, R-phycoerythrin, rhodamine, Texas red and lissamine. Fluorescein or rhodamine labeled α2-MG-, HA-, or TIMP-1-specific binding agents such as anti-α2-MG, anti-HA, or anti-TIMP-1 antibodies, or fluorescein- or rhodamine-labeled secondary antibodies can be useful in the invention. Useful fluorescent antibodies can be obtained commercially, for example, from Tago Immunologicals (Burlingame, Calif.) as described further below.

Radioimmunoassays (RIAs) also can be useful in the methods of the invention. Such assays are well known in the art. For example, Brophy et al., *Biochem. Biophys. Res. Comm.* 167:898-903 (1990)), describes a radioimmunoassay for detection of TIMP-1, and Pharmacia makes a radiometric assay for quantitation of HA using an $^{125}$I-labelled HA-binding protein (Guechot et al., *Clin. Chem.* 42:558-563 (1996). Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of α2-MG, HA, TIMP-1 or YKL-40 or another fibrotic marker can be performed using a spectrophotometer such as an EMAX Microplate Reader (Molecular Devices; Menlo Park, Calif.) in accordance with the manufacturer's instructions. It is understood that the assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, *Electrophoresis* 18:2184-93 (1997), and Bao, *J. Chromatogr. B. Biomed. Sci.* 699:463-80 (1997). Liposome immunoassays, such as flow-injection liposome immunoassays and liposome immunosensors, also can be used to detect α2-MG, HA, or TIMP-1 or to determine a level of α2-MG, HA, or TIMP-1 or another fibrotic marker according to a method of the invention (Rongen et al., *J. Immunol. Methods* 204:105-133 (1997)).

Sandwich enzyme immunoassays also can be useful in the methods of the invention. In a two-antibody sandwich assay, a first antibody is bound to a solid support, and the antigen is allowed to bind to the first antibody. The amount of α2-MG, HA, TIMP-1, or another fibrotic marker antigen is quantitated by measuring the amount of a second antibody that binds the fibrotic marker.

As an example, a two-antibody sandwich immunoassay can be useful to determine a level of TIMP-1 as described in Murawaki et al., supra, 1993. Briefly, serum (25 µl) is diluted 41-fold with 10 mM sodium phosphate buffer, pH 7.0 (1.0 ml). The diluted sample (20 µl) is mixed with 0.3 ml of 10 mM sodium phosphate buffer, pH 7.0, containing 50 ng/ml monoclonal antibody (Fab of clone 7-6C1) labeled with horseradish peroxidase, 1% bovine serum albumin, 0.1% Tween 20, 0.1 M NaCl and 0.005% thimerosal. A 0.1 ml aliquot of the mixed solution is transferred to each microplate well previously coated with a second monoclonal antibody (clone 7-23G9) having a different epitope specificity, and the plate incubated for 30 minutes at room temperature without shaking. The plate is washed three times with 0.3 ml 10 mM sodium phosphate buffer, pH 7.0, containing 0.1% Tween 20 and 0.1 M NaCl. Peroxidase activity bound to the plate is assayed by a 15 minute incubation at room temperature with 0.1 ml 0.15 M citric acid sodium phosphate buffer, pH 4.9, containing 0.5 mg/ml o-phenylenediamine and 0.02% $H_2O_2$. After stopping the reaction by addition of 0.1 ml 2 N $H_2SO_4$, the absorbance at 492 nm is measured in a microplate reader using a standard of human serum TIMP-1. Linearity between the amount of TIMP-1 and absorbance at 492 nm is demonstrated by graphing with logarithmic scales and yields an assay range of about 1.5 to 300 µg/well.

Quantitative western blotting also can be used to detect α2-MG, HA, or TIMP-1 or to determine a level of α2-MG, HA, or TIMP-1 or a level of another fibrotic marker antigen in a method of the invention. Western blots can be quantitated by well known methods such as scanning densitometry. As an example, protein samples are electrophoresed on 10% SDS-PAGE Laemmli gels. Primary murine monoclonal antibodies, for example, against human α2-MG, HA, or TIMP-1 are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669-675 (1998).

Sources for Antibodies

As described herein above, immunoassays including but not limited to enzyme-linked immunosorbent assays, radioimmunoassays and quantitative western analysis, can be useful in the diagnostic methods of the invention. Such assays rely on one or more antibodies, for example, anti-α2-MG, anti-HA, or anti-TIMP-1 antibodies. As used herein, the term "antibody" is used in its broadest sense to include polyclonal and monoclonal antibodies, as well as polypeptide fragments of antibodies that retain binding activity for α2-MG, HA, TIMP-1, or the relevant fibrotic marker antigen of at least about $1 \times 10^5$ $M^{-1}$. One skilled in the art understands that antibody fragments such as anti-α2-MG, anti-HA, and anti-TIMP -1 antibody fragments and including Fab, F(ab')$_2$ and Fv fragments can retain binding activity for the relevant fibrotic marker antigen and, thus, are included within the definition of the term antibody as used herein. Methods of preparing monoclonal and polyclonal antibodies are routine in the art, as described, for example, in Harlow and Lane, supra, 1988.

The term antibody, as used herein, also encompasses non-naturally occurring antibodies and fragments containing, at a minimum, one $V_H$ and one $V_L$ domain, such as chimeric antibodies, humanized antibodies and single chain Fv fragments (scFv) that specifically bind α2-MG, HA, TIMP-1 or the relevant fibrotic marker antigen. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), Antibody Engineering (Second edition) New York: Oxford University Press (1995).

A variety of useful anti-α2-MG, anti-HA, and anti-TIMP-1 monoclonal and polyclonal antibodies are well known in the art and, in many cases, are commercially available. For example, a nephelometry assay for α2-macroglobulin is available from Beckman Coulter (kit #449430), and affinity purified goat anti-human α2-MG and peroxidase-labeled goat anti-human α2-MG antibodies suitable for ELISA and western blotting are available, for example, from Cedarlane Laboratories Limited (CL20010AP and CL20010APHP) and Affinity Biologicals Incorporated (GAA2M-AP and GAA2M-APHRP). Similarly, affinity purified sheep anti-HA antiserum can be obtained from Biotrend (#5029-9990).

Anti-human TIMP-1 antibodies also are readily available from a variety of commercial sources. For example, the anti-human TIMP-1 monoclonal antibody 147-6D11 is suitable for ELISA or western blotting analysis and can be obtained from Medicorp, Inc. (Montreal, Canada), and the anti-human TIMP-1 monoclonal antibody MAB970 is available from R&D Systems, Inc., for use, for example, in western blotting or sandwich ELISA assays. MAB970 can be combined, for example, with biotinylated anti-human TIMP-1 antibody (BAF970) from R&D Systems, Inc., for detection of TIMP-1 by sandwich ELISA. In addition, rabbit anti-human TIMP-1 polyclonal antiserum and mouse anti-human monoclonal antibodies suitable, for example, for western blotting with enhanced chemiluminescence detection can be obtained from Research Diagnostics Inc. (RDI-TIMP1abr and RDI-TIMP1-C1).

Assays for Activity

As discussed above, assays based on the activity of a fibrotic marker also can be useful for detecting α2-MG, HA or TIMP-1 or for determining a level of α2-MG, HA or TIMP-1 or another fibrotic marker and, therefore, are useful in the methods of the invention. As an example, a variety of assays for α2-MG activity can be useful for detecting α2-MG or determining a level of α2-MG in a sample in a method of the invention. Because α2-MG-bound proteases display inhibited proteolytic activity but retain the ability to hydrolyze amide and ester bonds of small substrates, α2-MG can be detected, or a level determined, by assaying for inhibition of trypsin, subtilisin, chymotrypsin, plasmin, elastase, thermolysin, or papain activity or the activity of another target protease without inhibition of amidolytic activity. Substrates such as labeled casein or labeled fibrin can be useful for assaying for inhibition of target protease activity. Furthermore, based on its broad protease substrate specificity, a level of α2-MG can be determined by assaying for inhibition of the activity of two or more target proteases using, for example, $^{14}C$-casein and $^{125}I$-fibrin (Armstrong et al., supra, 1999). α2-MG also can be detected or a level of α2-MG determined based on the ability of α2-MG to shield a bound protease from an antibody or a high molecular weight inhibitor. Following reaction of a sample with, for example, trypsin and then trypsin inhibitor, residual trypsin activity is assayed with a low molecular mass substrate such as the amide BApNA (Ganrot, supra, 1966; Armstrong et al., supra, 1985). Trypsin activity following treatment with trypsin inhibitor is indicative of α2-MG. These and other well known assays for α2-MG activity can be useful in the methods of the invention.

Similarly, assays for TIMP-1 activity are well known in the art. In particular, one assays for the ability to inhibit protease activity of a matrix metalloproteinase, for example, using reverse gelatin zymography. Reverse gelatin zymography is performed by including a gelatinase such as gelatinase A in a gel mix with the gelatin substrate. Conditioned media, such as conditioned media from baby hamster kidney cells can be used as a convenient source of gelatinase. Plasma samples are electrophoresed, and the resulting pattern analyzed, for example, with scanning digitization using a Hewlett Packard scanner. TIMP-1 activity is observed as a reduction of gelatin degradation. See, for example, Kossakowska et al., supra, 1998. The skilled person recognizes that these and other routine assays for TIMP-1 activity can be useful in the methods of the invention.

Additional Markers

It is clear that the methods of the invention can be practiced, if desired, by detecting the three markers α2-MG, HA and TIMP-1 without assaying for any additional markers or evaluating any other clinical or echographic characteristics. In addition, these three assays can be used as a panel in combination with one or more additional fibrotic marker assays or evaluation of one or more clinical or echographic variables. In specific embodiments, the invention provides a method of diagnosing the presence or severity of liver fibrosis in an individual by detecting α2-MG, HA and TIMP-1 in a sample and also detecting at least one of the following markers: PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 or ApoB. In one embodiment, a method of the invention for diagnosing the presence or severity of liver fibrosis includes the steps of detecting α2-MG, HA, and TIMP-1 in a sample. In a further embodiment, a method of the invention is limited to detecting α2-MG, HA, and TIMP-1, and no additional fibrotic markers are detected.

In view of the above, it is clear that assays for one or more additional biochemical or serological markers of fibrosis or evaluation of one or more clinical or echographic variables associated with fibrosis can be combined with detection of α2-MG, HA, and TIMP-1 to diagnose the presence or severity of liver fibrosis. Examples of additional biochemical and serological markers include, yet are not limited to, PIIINP, laminin, tenascin, collagen type IV, collagen type VI, YKL-40, MMP-3, MMP-2, MMP-9/TIMP-1 complex, sFas ligand, TGF-.beta.1, IL-10, apoA1, apoA2 and apoB. Additional biochemical and serological markers useful in the invention include, without limitation, fibronectin, pseudocholinesterase, manganese superoxide dismutase, N-acetyl-β-glucosaminidase (β-NAG), glutathione peroxidase, connective tissue growth factor (CTGF); platelet derived growth factor (PDGF), PDGF receptor, inducible nitric oxide synthetase, nitrotyrosine, bilirubin, ferritin and α-fetoprotein, γ-glutamyl transpeptidase (GGT), aspartate aminotransferase (AST), alanine aminotransferase (ALT), AST/ALT ratio, albumin, γ-globulins, βγ-block, prothrombin index, Child-Pugh score, PGA index (prothrombin time, GGT concentration and apoA1 concentration), PGAA index (PGA score with α2-macroglobulin level), hemoglobin, mean corpuscular volume, lymphocyte count, cholesterol, urea, creatinine, sodium and platelet count.

A clinical or echographic variable also can be a fibrotic "marker" useful in the methods of the invention. Thus, analysis of one or more clinical or echographic variables can be combined with detection of α2-MG, HA and TIMP-1 to diagnose the presence or severity of liver fibrosis, or another fibrotic disorder as described hereinabove. As examples, such a clinical variable can be patient age or gender or the presence of palmar erythema, Dupuytren's contracture, finger clubbing, spider nevi, firm liver, splenomegaly or collateral circulation. Echographic variables useful in a method of the invention include, for example, liver length (right kidney), irregular liver surface, liver heterogeneity, spleen length, ascites or collateral circulation. See, for example, Oberti et al., Gastroenterol. 113:1609-1616 (1997). It is understood that the analysis of these and other well known clinical or echographic variables can be useful in a method of the invention. Furthermore, a method of the invention encompasses determination of the clinical or echographic variable, for example, liver palpation, or can rely on one or more historic, or previously determined clinical or echographic variables.

Assays for detection of biochemical or serological markers useful in the invention are well known in the art and in many cases commercially available. Such assays include, but are not limited to, amplification based methods such as RT-PCR and other methods for quantitative analysis of RNA levels; immunoassays such as radioimmunoassays, enzyme-linked assays, two-antibody sandwich assays and quantitative western analysis; and assays for biological activity such as enzyme activity. Assays for PIIINP, laminin, tenascin, collagen type IV, collagen type VI, YKL-40, MMP-3, MMP-2, MMP-9/TIMP-1 complex, sFas ligand, TGF-β1, IL-10, apoA1, apoA2 and apoB are commercially available from various sources as summarized in Table 1.

TABLE 1

COMMERCIAL SOURCES FOR FIBROTIC MARKER ASSAYS

| Marker | Company | Assay | Catalog number |
|---|---|---|---|
| PIIINP | Orion Diagnostica (Espoo, Finland) | RIA | 05903 |
| laminin | Chemicon Intl. (Temecula, CA) | ELISA | ECM310 |
| enascin | Chemicon Intl. (Temecula, CA) | ELISA | ECM320 |
| collagen IV | Iatron Laboratories (Tokyo, Japan) | RIA | KCAD1 |
| YKL-40 | Metra Biosystems (Mountain View, CA) | ELISA | 8020 |
| MMP-3 | Amersham Pharmacia (Piscataway, NJ) | ELISA | RPN 2613 |
| MMP-2 | Amersham Pharmacia (Piscataway, NJ) | ELISA | RPN 2617 |
| MMP-9/TIMP-1 complex | SBA Sciences (Turku, Finland) | ELISA | MP2215 |
| sFas ligand | Bender MedSystems Diagnostics (Vienna, Austria) | ELISA | BMS260/2 |
| TGF-β1 | R&D Systems (Minneapolis, MN) | ELISA | DB100 |
| IL-10 | R&D Systems (Minneapolis, MN) | ELISA | HS100B |
| apoA1 | AlerChek, Inc. (Portland, ME) | ELISA | A70101 |
| apoA2 | AlerChek, Inc. (Portland, ME) | ELISA | A70102 |

TABLE 1-continued

COMMERCIAL SOURCES FOR FIBROTIC MARKER ASSAYS

| Marker | Company | Assay | Catalog number |
|---|---|---|---|
| apoB | Sigma Diagnostics (St. Louis, MO) | T* | 357-A |

*designates immunoturbidimetric

Assays for additional biochemical or serological markers that can be combined with detection of α2-MG, HA and TIMP-1 in a method of the invention also are well known in the art. Fibronectin, for example, can be conveniently assayed by turbidimetric assay available from Roche Diagnostics (Mannheim, Germany). Pseudocholinesterase (PCHE) can be assayed using standard methodology available from Boehringer. Levels of N-acetyl-β-glucosaminidase (β-NAG) can be determined by assaying for enzymatic activity using a kit available from Cortecs diagnostics. Manganese superoxide dismutase (Mn-SOD) levels can be conveniently determined by ELISA using a kit available, for example, from Bender MedSystem. Glutathione peroxidase levels can be determined by assaying for enzymatic activity using, for example, a kit available from Randox Laboratories Ltd. (Oceanside, Calif.).

Total or direct bilirubin, GGT, AST and ALT levels can be determined using an autoanalyser such as Hitachi 917 Automate (Mannheim, Germany) with Roche Diagnostics reagents. Albumin levels can be determined, for example, by the bromocresol green method as described in Doumas et al., *Clin. Chim Acta* 31:87-96 (1971), and ferritin and α-fetoprotein levels can be conveniently determined using, for example, an immunoassay available from Boehringer. In addition, levels of $\alpha_1$ globulin, $\alpha_2$ globulin, β globulin and γ-globulin can be determined, for example, by serum protein electrophoresis in an automatic system (Hydrasys and Hyrys, Sebia; Issy-Les-Moulineaux, France). Methods of determining prothrombin activity also are well known in the art and include the clotting method available from Organon Technika (West Orange, N.J.). PGA index can be determined as described in Poynard et al., *Gastroenterol.* 100:1397-1402 (1991), and PGAA index also can be determined by well known methods as described in Naveau et al., *Dig. Dis. Sci.* 39:2426-2432 (1994)).

Platelet counts, lymphocyte counts, mean corpuscular volume and related variables can be determined by a variety of methodologies using, for example, a Bayer-Technicon H2 analyser (Bayer-Technicon Instruments; Tarrytown, N.Y.). Cholesterol levels can be determined by standard methodologies available, for example, from Boehringer. Thus, it is clear to the skilled person that a variety of methodologies, including but not limited to the above, are well known in the art and can be useful in the diagnostic methods of the invention.

The following examples are intended to illustrate but not limit the present invention.

EXAMPLE I

Assays for β2-Macroglobulin, Hyaluronic Acid and Tissue Inhibitor of Metalloproteinases-1

A. Quantitation of Human α2-Macroglobulin (α2-MG)

Serum levels of human α2-macroglobulin were quantitated using the Beckman Array.RTM. 360 System as follows to determine α2-MG levels in the range of 0.75-270 mg/ml.

The Beckman Array® 360 system was used for determination of α2-MG concentrations. This system utilizes a nephelometer which measures the rate of light-scatter formation resulting from an immunoprecipitation reaction between α2-MG antigen in a sample with antibody to human α2-MG. After passing a beam of light through the solution in a flow cell, the intensity of light scattered by the formed macromolecular particles of insoluble complexes suspended in solution is detected and measured by the nephelometer. The increase in light scatter resulting from the antigen-antibody reaction is converted to a peak rate signal proportional to the α2-MG concentration in the sample. The resulting formation of complexes and the consequent change in the intensity of scattered light occurs at a rate that increases gradually at first, then rapidly, and finally proceeds through a peak rate of change for the component being analyzed.

Serum samples were drawn from fasting individuals and generally physically separated from cells within 2 hours from the time of collection as set forth in NCCLS publication H 18-A. Samples not assayed within 72 hours were stored frozen at –15° C. to –20° C. Frozen samples were at most thawed one time. Grossly hemolyzed, highly lipemic or turbid specimens were rejected for further analysis.

Reagents were removed from storage at 4° C. and used immediately. Buffers and Diluents were mixed thoroughly by inversion prior to being added to the instrument. Set-up, priming and calibration were performed according to the manufacturer's instructions with samples diluted 1:36. Relatively concentrated samples such as undiluted samples or 1:6 dilutions were generally avoided. Grossly lipemic sample were diluted 1:2 with diluent before assaying. Dust particles or other particulate matter, which can result in extraneous light-scattering signals, in the reaction solution were avoided. Prior to assaying samples, any air bubbles or foam in the sample cups and reagent bottle were removed by using a disposable transfer pipette or pipette tip to aspirate the bubbles. DTT was avoided in the work area.

Samples were analyzed for α2-MG concentration as follows. The Reagent Wheel (left wheel) on the instrument was loaded with AMG antiserum in space #2. Dilution segments were loaded with 150.mu.L of control or sample in the wells on the larger side of the fan shaped segments. Segments and initial dilution control/sample cups were marked for identification. Bubbles were avoided while controls and serum samples were loaded.

Vigil® Protein Control Levels 1 and 3 (3 drops) was placed in cups 1 and 3, respectively. Biorad Liquichek®. Immunology Control Level 2 (150 μL) was placed in cup 2. Patient samples (150 μL) were added to sequential cups. Segments were placed on right wheel beginning at position #1. Evaporation covers were placed over Reagent and Sample Wheels.

On the Master Screen menu, the RESULTS RECALL (F3) was selected before (F4) CLR CUR RUN. After returning to the MASTER SCREEN, the SAMPLE PROGRAM (F1) was selected. ENTER was selected when Reagent wheel #1 appeared and at each cup number. The control ID or sample Acc.# was entered. Test "2" was selected, and SAVE CUP (F1) was selected for each cup. START was selected to begin the analysis. At the end of the run, (Y) was selected in response to CLEAR CURRENT RUN & START NEXT RUN.

Results were reported by the Beckman Array® 360 in mg/dl using whole numbers in the Pros System. Samples were diluted routinely by the instrument 1:36. Samples greater than 750 mg/dl were assayed at a 1:216 dilution by the instrument. Samples having a concentration less than 75 mg/dl at a 1:36 dilution are reported as <75 mg/dl. At initial dilutions the Beckman analytical range was 75-750 mg/dl, while the extended range was 75-27,000 mg/dl. The range for normal individuals as verified at Prometheus Laboratories was 103-274 mg/dl.

Quality control was performed as follows. Three levels of controls were used: low, medium and high. Controls were within 2 standard deviations, except that runs were accepted with two controls within 2 standard deviations and the third control between 2 and 3 standard deviations. The controls used were Beckman Vigil I and III and Biorad Level II. Controls were assayed with each sample run.

The assay is calibrated every 14 days, and also when changes in reagent lots occur or when a major change has occurred in the instrument. Linearity is confirmed every 6 months with appropriate linearity material. This is done to ensure consistent performance over time and to comply with State and National standards.

Assay calibration verification is performed every 6 months to ensure consistency over time. A minimum of five verification samples including minimum, mid-point, and maximum concentrations are evaluated every 6 months. The coefficient of variation (% CV) of the verification sample results must be less than 15% in order to report out patient sample results.

B. Quantitation of Hyaluronic Acid (HA)

Serum levels of HA were determined using the Hyaluronic Acid (HA) Quantitative test kit (Catalog #029001) from Corgenix essentially as follows.

Serum samples were stored at −70° C. Multiple freeze/thaw cycles were avoided, with a maximum of 4 freeze/thaw cycles per sample. The kits were stored at 2-8° C.

Prior to use, the kit and patient samples were equilibrated to room temperature (18-28° C.). The pouch of coated strips also was equilibrated to room temperature before opening. Wash solution (0.01 M PBS, pH 7.35+/−0.1) was prepared by diluting the 33×PBS wash concentrate with distilled water and adjusting the pH of the final solution to pH 7.35+/−0.1.

All blanks, standards, controls and samples were assayed in duplicate. A water blank for calibration of the spectrophotometer was included with each plate and remained empty until addition of 200 µl water immediately prior to reading. Reaction buffer without serum sample was used-for the reagent blank, which represented the 0 ng/ml HA reference solution, and was treated the same as patient samples and reference solutions in subsequent assay steps. Three known patient samples (low, middle and high) were run with each assay. In addition, 50 ng/ml HA, 100 ng/ml HA, 200 ng/ml HA, 500 ng/ml HA and 800 ng/ml HA reference solutions supplied with each kit were assayed as described further below.

HA reference solutions and patient samples were diluted 1:11 by addition of 25 µl reference solution or sample to 250 µl of reaction buffer and mixed by gentle vortexing. The diluted reference, samples and controls were added (100 µl) to each well. The water blank remained empty. The plate was covered and incubated for 60 minutes at room temperature. After the incubation was complete, the contents of the wells were removed by aspiration. Plates were washed four times with 1.times. wash solution while avoiding the plates drying out between washes. The plate was blotted vigorously on paper towels to remove residual buffer after the last wash.

HRP-conjugated HA binding protein solution (100 µl) was added to all wells except the water blank before covering the plate and incubating for 30 minutes at room temperature. After the incubation was complete, the plate was washed four times as described above. Substrate solution (100 µl 3,3',5,5'-tetramethylbenzidine and hydrogen peroxide, stabilized) was then added to each well except for the water blank. The covered plate was then incubated for 30 minutes at room temperature. The plate was kept in the dark.

The $OD_{650}$ of the 800 ng/ml HA standard was determined. For an OD less than 0.500, the substrate incubation was continued and the OD monitored to determine if the OD had reached 0.500. For an OD greater than 0.500 or after one hour of substrate incubation even if the OD had not reached 0.500, the reactions were terminated by addition of 100 µl of Stopping Solution (0.36 N sulfuric acid) to each well except the water blank. The stop solution was added in the same order and at approximately the same rate as addition of the substrate solution. Before reading the optical densities, 200 µl distilled water was added to the water blank. The OD of each well was read at 450 nm (650 nm reference) within one hour after "zeroing" the plate reader against the water blank.

The following criteria were used to determine if the assay was reliable. The mean OD value of the reagent blank (zero standard) was less than 0.10. Readings greater than 0.10 were considered indicative of possible substrate or reagent contamination, and results were not reported under these conditions. The mean OD value of the 500 ng/ml HA reference was 0.800 or greater. Controls for the three known patient samples were within the following ranges: Low control: 78.6 to 117.2 ng/ml. Mid control: 148.5 to 214.1 ng/ml. High control: 297.8 to 460.7 ng/ml. Samples with HA concentrations greater than 800 ng/ml were further diluted and assayed a second time to obtain a more accurate result.

The known patient controls and samples were determined from a standard 4-parameter curve generated using Softmax and reported in ng/ml. The patient values were not reported if the concentration exceeded the concentration of the highest standard. For patient values greater than the concentration of the highest standard at a 1:11 dilution, samples were assayed at a 1:55 dilution and, if necessary, at higher dilution.

The HA ELISA assay is evaluated every six months to ensure consistent performance over time. A minimum of five samples with previously known HA values are evaluated in a blinded fashion to the operator. For the assay performance to be acceptable, results for negative samples must be negative, and results for positive samples must be positive and yield results within 15% of the previously obtained values. If greater than 20% of the validation samples fail the performance criteria, troubleshooting is implemented, and the assay is not used to report patient data until acceptable assay performance are reestablished.

C. Quantitation of Tissue Inhibitor of Metalloproteinases-1 (TIMP-1)

Serum levels of TIMP-1 were determined using the Biotrak® test kit (Catalog# RPN2611) from Amersham Pharmacia Biotech (Piscataway, N.J.) essentially as follows.

Kit contents were thawed and equilibrated to 20-25° C. Serum samples were stored frozen at −70° C. Repeated freeze-thaw cycles of the samples were minimized, with a maximum of six freeze-thaw cycles.

Assay reagents were prepared as follows and stored at 2-8° C. for at most 7 days. Assay buffer 1 (0.1 M phosphate buffer, pH 7.5, with 0.9% (w/v) sodium chloride, 0.1% (w/v) BSA and 0.1% Tween-20) was prepared by adding distilled water to the assay buffer concentrate and adjusting the final volume to 100 ml.

Anti-TIMP-1 horseradish peroxidase conjugate was prepared in assay buffer 1 essentially as follows. To the stock bottle containing lyophilized conjugate, 11 ml diluted assay buffer 1 was added; the contents were mixed gently until completely dissolved while avoiding vigorous agitation and foaming. Wash buffer (0.1 M phosphate buffer, pH 7.5, containing 0.05% Tween-20) was prepared by adding distilled water to the wash buffer concentrate and bringing the final volume to 500 ml, followed by thorough mixing.

The 100 ng/ml TIMP-1 stock solution was prepared as follows and stored at 2-8° C. The lyophilized TIMP-1 standard was reconstituted in 0.1 M phosphate buffer, pH 7.5, containing 0.9% (w/v) sodium chloride, 0.1% (w/v) bovine serum albumin and 0.1% Tween-20 to make a standard TIMP-1 stock solution of 100 ng/ml. The contents were mixed gently until completely dissolved without vigorous agitation or foaming. Additional standards (1.565, 3.13, 6.25, 12.5, 25 and 50 ng/ml) for a standard curve were prepared fresh before each assay by two-fold serial dilution of the 100 ng/ml stock solution into assay buffer 1 in 1.2 ml dilution tubes. A zero standard (blank) was also prepared.

The pouch containing the microtiter plate was opened after equilibration to room temperature. All samples and standards were assayed in duplicate, and standards for a standard curve were present on each plate. On each plate, seven standards, two controls and a maximum of different 39 samples were present in duplicate.

Samples were diluted 1:120 in tubes by mixing 595 µl assay buffer 1 with 5 µl serum. The dilutions were mixed by vortexing. Using a multichannel pipettor, 100 µl of blank, standards and diluted samples were added to individual wells on a microtiter plate. The plate was covered with the lid provided and incubated at room temperature for exactly two hours. Following the two hour incubation, the contents of the wells were aspirated, and each well was washed four times with wash buffer, with complete filling and aspiration of the wells after each wash. After the final wash, the plates were blotted on paper towels to remove residual wash buffer.

Peroxidase conjugate (100 µl) was added to each well using a multichannel pipettor, and the covered plate incubated at room temperature for exactly two hours. After the incubation, the wells were aspirated and washed as before. Immediately upon conclusion of the incubation, 100 µl of room temperature equilibrated TMB substrate (3,3',5,5'-tetramethylbenzidine/hydrogen peroxide in 20% (v/v) dimethylformamide) was added to each well. The plates were covered and incubated for exactly 30 minutes at room temperature. In some cases, the reactions were monitored at 630 nm. The reactions were stopped by addition of 100 µl 1 M sulfuric acid to all wells. Absorbance was determined at 450 nm within 30 minutes.

Control and patient samples values were determined using a standard curve (4-parameter curve fit) generated using Softmax. Concentration values from the standard curve were multiplied by the dilution factor (120) to obtain actual concentrations, reported in ng/ml. Quality of the assay was confirmed using known serum samples. The low control was in the range of 668.1 to 979.9 ng/ml. The high control was in the range of 2677.9 to 3300.2 ng/ml. Patient values generally did not exceed the concentration in ng/ml of the highest standard. Where the patient value was greater than the concentration of the highest standard at a 1:120 dilution, the result was reported as greater than 120 times the concentration of the highest standard.

The TIMP-1 ELISA assay is validated every six months to ensure consistent performance over time. A minimum of five samples with previously known values are evaluated in a blinded fashion to the operator. Results for negative samples must be negative. Results for positive samples must be positive and must yield results within 15% of the previously obtained values. Where greater than 20% of the validation samples fail the performance criteria, troubleshooting is implemented. Further patient data are not reported until acceptable assay performance is reestablished.

EXAMPLE II

An algorithm was developed to differentiate no/mild from moderate/severe fibrosis in chronic HCV patients, as determined histologically from a liver biopsy, and staged using the Metavir system summarized in Table 2.

TABLE 2

| Fibrosis | Metavir stage | Description |
|---|---|---|
| No/mild | F0 | No fibrosis |
| | F1 | Stellate enlargement of portal tract without septa formation |
| Moderate/severe | F2 | Enlargement of portal tract with rare septa formation |
| | F3 | Numerous septa without cirrhosis |
| | F4 | Cirrhosis |

Serum samples from 696 chronic HCV patients were obtained, at or near the time of liver biopsy, from 4 study sites. Levels of the three markers of fibrosis, hyaluronic acid (HA), tissue inhibitor of metalloproteinase-1 (TIMP-1), and α2-macroglobulin (α2M, or A2M), were determined in each specimen by protein binding assay (HA), ELISA (TIMP-1) and nephelometry (A2M). Severity of fibrosis in patients was staged by histological staining of a biopsy specimen using the Metavir system. These variables were subjected to regression analysis to derive the predictive algorithm (below) constructed from the concentrations of the markers and their regression coefficients.

$$\text{Index} = \frac{\text{Exp}^{[-4.3633+(0.0108*\text{HA ng/ml})+(0.0015*\text{TIMP-1 ng/ml})+(0.5357*\text{A2M mg/ml})]}}{1 + \text{Exp}^{[-4.3633+(0.0108*\text{HA ng/ml})+(0.0015*\text{TIMP-1 ng/ml})+(0.5357*\text{A2M mg/ml})]}}$$

The following results were obtained. An index cutoff value of 0.42 was determined. That is, a patient index value less than 0.42 was determined to be a negative result, i.e., consistent with no/mild fibrosis or a staging of F0-F1 on the Metavir scale. A patient index value greater than 0.42 was determined to be a positive result, i.e., consistent with moderate/severe fibrosis or a staging of F2-F4 on the Metavir scale. Thus, the algorithm does not contain indeterminate values.

Figure 4:
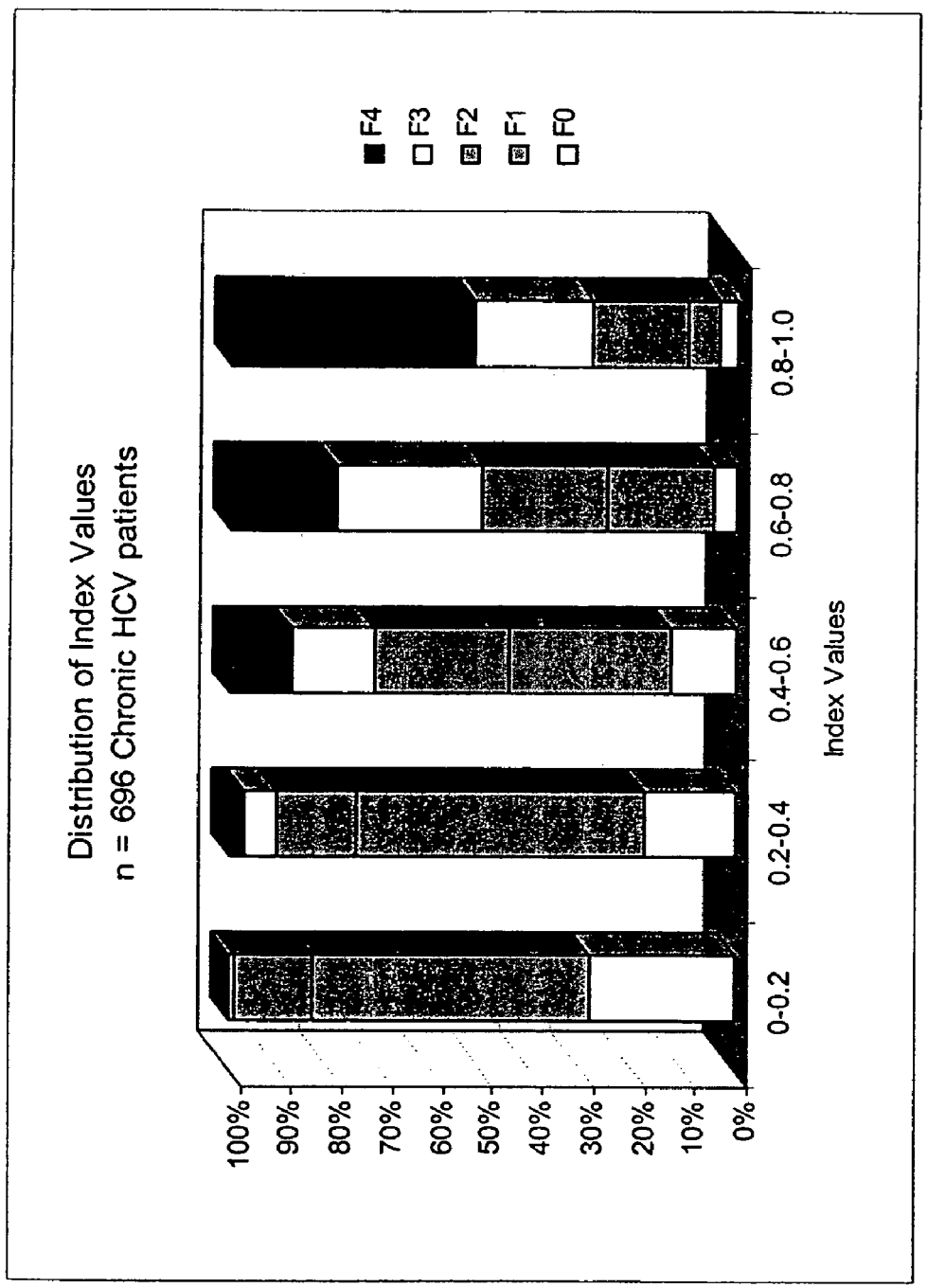
FIG. 4 provides a graph showing index values from the three marker algorithm.

Using an index cutoff of 0.42, each sample was classified as negative (<0.42) or positive and compared with the fibrosis stage by biopsy to determine the performance of the algorithm to predict moderate/severe fibrosis. Index values are shown in FIGS. 3 and 4 and Table 3.

TABLE 3

| | F0 | F1 | F2 | F3 | F4 | | F0 | F1 | F2 | F3 | F4 |
|---|---|---|---|---|---|---|---|---|---|---|---|
| Test+ | 25 | 71 | 91 | 88 | 111 | 386 | 27.5% | 29.0% | 65.5% | 85.4% | 94.1% |
| Test− | 66 | 174 | 48 | 15 | 7 | 310 | 72.5% | 71.0% | 34.5% | 14.6% | 5.9% |
| Subtotal | 91 | 245 | 139 | 103 | 118 | 696 | | | | | |
| Indeterm | 0 | 0 | 0 | 0 | 0 | 0 | 0.0% | 0.0% | 0.0% | 0.0% | 0.0% |
| Total | 91 | 245 | 139 | 103 | 118 | 696 | | | | | |

Figure 5:
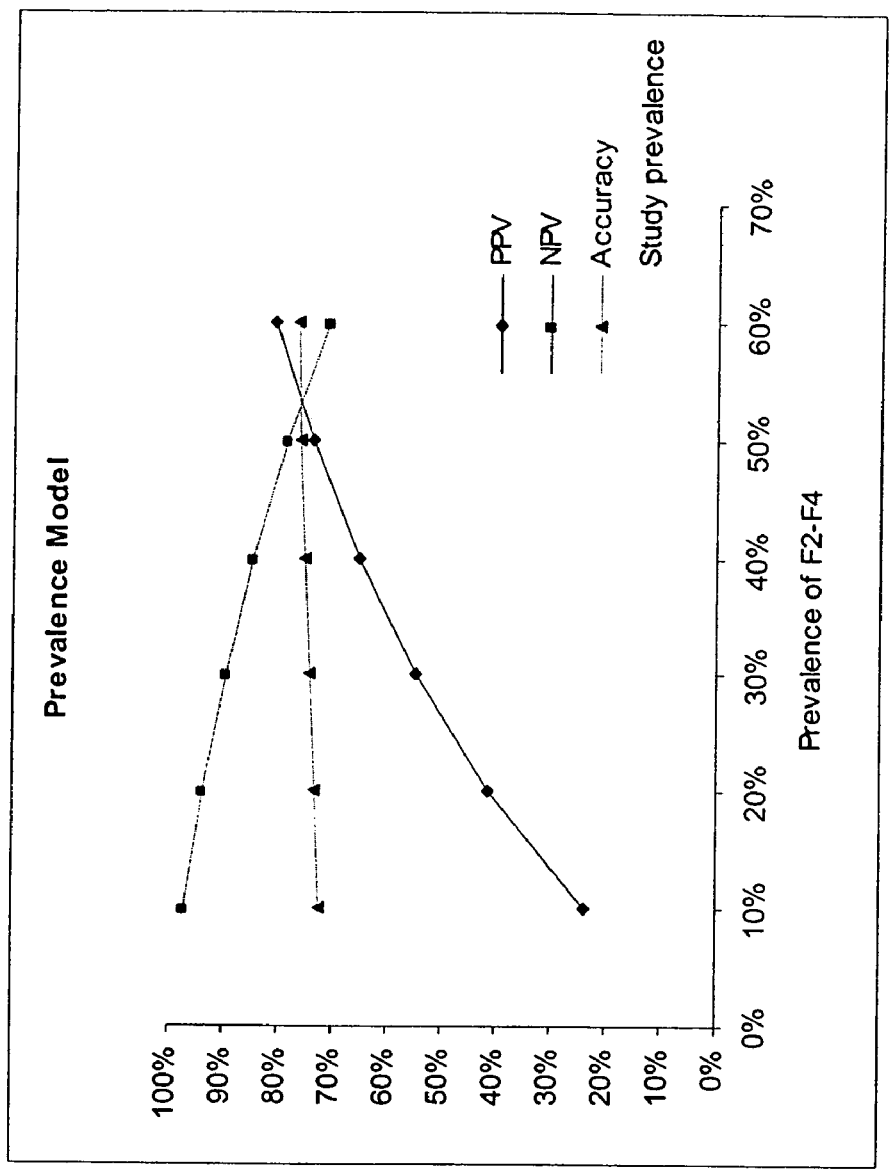
FIG. 5 provides a prevalence model for the three marker algorithm.

The performance of the algorithm in differentiating F0-F1 from F2-F4 liver disease was determined. The diagnostic value of the algorithm was assessed by determining the area under the receiver operating characteristic (ROC) curve. (Area under ROC curve: 0.827±0.0154 (SE)). The algorithm performance is depicted in Table 4. A prevalence model for the algorithm is shown in FIG. 5.

TABLE 4

|  | F2-F4 | F0-F1 |  | F3-F4 | F0-F2 |  |
|---|---|---|---|---|---|---|
| Test+ | 290 | 96 | 386 | 199 | 187 | 386 |
| Test− | 70 | 240 | 310 | 22 | 288 | 310 |
| Subtotal | 360 | 336 | 696 | 221 | 475 | 696 |
| Indeterm | 0 | 0 | 0 | 0 | 0 | 0 |
| Total | 360 | 336 | 696 | 221 | 475 | 696 |
| Prev | 51.7% | 95% Cl |  | 31.8% | 95% Cl |  |
| Sens | 80.6% | 76.1% | 84.6% | 90.0% | 85.3% | 93.7% |
| Spec | 71.4% | 66.2% | 76.2% | 60.6% | 56.1% | 65.1% |
| PPV | 75.1% | 70.5% | 79.4% | 51.6% | 46.4% | 56.7% |
| NPV | 77.4% | 72.3% | 81.9% | 92.9% | 89.5% | 95.5% |
| Accuracy | 76.1% | 72.8% | 79.3% | 70.0% | 66.4% | 73.3% |
| Indeterm | 0.0% |  |  | 0.0% |  |  |

EXAMPLE 3

A second algorithm was determined using two markers: HA and TIMP1. The HA and TIMP1 levels from Example 2 were used in this algorithm. As for the three marker test above, sensitivity was maintained at 80%. Results are shown in Tables 5 and 6. With the two marker analysis and sensitivity of 80%, specificity of the test was 63.4%. In contrast, when A2M levels were analyzed with HA and TIMP1 levels as above, specificity of the test was 71.4%. Thus, addition of the A2M marker to the analysis improved the specificity of the test.

TABLE 5

|  | F0 | F1 | F2 | F3 | F4 |  |
|---|---|---|---|---|---|---|
| Test+ | 35 | 88 | 84 | 90 | 115 | 412 |
| Test− | 56 | 157 | 55 | 13 | 3 | 284 |
| Total | 91 | 245 | 139 | 103 | 118 | 696 |

TABLE 6

|  | F2-F4 | F0-F1 | Total |
|---|---|---|---|
| Test+ | 289 | 123 | 412 |
| Test− | 71 | 213 | 284 |
| Total | 360 | 336 | 696 |
| Prev | 51.7% |  |  |
| Sens | 80.3% |  |  |
| Spec | 63.4% |  |  |
| PPV | 70.1% |  |  |
| NPV | 75.0% |  |  |
| Accuracy | 72.1% |  |  |

EXAMPLE 4

Use of HA, TIMP1, and A2M as Markers of Liver Fibrosis and as Predictors of Clinical Outcome in Patients with Primary Biliary Cirrhosis (PBC)

Twenty-nine paired serum and liver biopsy specimens were obtained from 10 patients with PBC. The patients were enrolled in a randomized double-blind controlled trial of methotrexate vs. placebo for the treatment of PBC. All patients were on ursodiol. Samples were collected every two years over a 6-year period, along with detailed clinical data from protocol endoscopies, ultrasounds, and clinic visits. Each biopsy was scored by four independent pathologists on a four-point scale (0-none, 1-non-bridging fibrosis, 2-bridging fibrosis, 3-cirrhosis). Three serum markers of fibrosis (HA, TIMP1, and A2M) were measured by enzyme-linked immunosorbent assay. A serum fibrosis index was derived from the three biochemical markers, using the FIBROSpect II regression equation (Prometheus Labs, San Diego, Calif.). Clinical complication end points included the following events: development of esophageal varices, hepatic encephalopathy, ascites, and variceal bleeding.

Subjects who had a clinical event during the 8 year follow up had higher serum fibrosis indices than those who never had a clinical event. (Data not shown.) The serum fibrosis index correlated significantly with the histological fibrosis score. (Spearman r=0.49, p=0.007). Thus, the index was able to differentiate early vs. late fibrosis stage. (Data not shown.)

Thus, the serum fibrosis index can be used as a predictor of long-term clinical outcome in PBC and can also be used to differentiate early vs. late stage fibrosis in PBC.

All journal article, reference and patent citations provided above, in parentheses or otherwise, whether previously stated or not, are incorporated herein by reference in their entirety.

EXAMPLE 5

Use of HA, TIMP1, and A2M as Markers of Liver Fibrosis in Patients with Nonalcoholic Steatohepatitis (NASH)

Two hundred paired serum and liver biopsy specimens were obtained from patients with NASH and controls. Biopsies were scored using the Metavir scale or the Brunt scale. Three serum markers of fibrosis (HA, TIMP1, and A2M) were measured by enzyme-linked immunosorbent assay. A serum fibrosis index was derived from the three biochemical markers, using the FIBROSpect II regression equation (Prometheus Labs, San Diego, Calif.). An index cutoff value was determined using ROC analysis. The index cutoff value of 0.475 was used to distinguish between F0-F2 stage fibrosis and F3-F4 stage fibrosis. That is, a patient index value less than 0.475 was determined to be a negative result, i.e., consistent with no/mild/moderate fibrosis or a staging of F0-F2 on the Metavir scale. A patient index value greater than 0.475 was determined to be a positive result, i.e., consistent with moderate/severe fibrosis or a staging of F3-F4 on the Metavir scale. Thus, the algorithm does not contain indeterminate values. Results are shown in Table 7.

TABLE 7

| | Cutoff = 0.475 | | |
|---|---|---|---|
| | Biopsy | | |
| | F3-F4 | F0-F2 | |
| Test pos | 38 | 33 | 71 |
| Test neg | 9 | 120 | 129 |
| | 47 | 153 | 200 |
| Sensitivity | 80.9% | | |
| Specificity | 78.4% | | |
| PPV | 53.5% | | |
| NPV | 93.0% | | |
| Accuracy | 79.0% | | |

Although the invention has been described with reference to the examples provided above, it should be understood that various modifications can be made without departing from the spirit of the invention. Accordingly, the invention is limited only by the claims.

---

What is claimed is:

1. A method for diagnosing the presence or severity of liver fibrosis in an individual, the method comprising:
   (a) determining a level of α2-macroglobulin (α2-MG) in a sample from said individual by contacting said sample with an α2-MG-specific binding agent;
   (b) determining a level of hyaluronic acid (HA) in a sample from said individual by contacting said sample with an HA-specific binding agent;
   (c) determining a level of tissue inhibitor of metalloproteinases-1 (TIMP-1) in a sample from said individual by contacting said sample with a TIMP-1-specific binding agent;
   (d) calculating an index value for the individual using a regression algorithm based upon said level of α2-MG, HA, and TIMP-1, wherein said regression algorithm has a formula:

Index Value=Exp($b_0+b_1*x_1+b_2*x_2b_3*x_3$)/(1+Exp($b_0+b_1*x_1+b_2*x_2+b_3*x_3$)), wherein
   $b_0$ is an intercept value, wherein said intercept value is based upon the levels of α2-MG, HA, and TIMP-1 in a population of liver fibrosis patients;
   $b_1$ is a regression coefficient value for HA, wherein said regression coefficient value is based upon the level of HA in said population of liver fibrosis patients;
   $x_1$ is the concentration level of HA;
   $b_2$ is a regression coefficient value for TIMP-1, wherein said regression coefficient value is based upon the level of TIMP-1 in said population of liver fibrosis patients;
   $x_2$ is the concentration level of TIMP-1;
   $b_3$ is a regression coefficient value for α2-MG, wherein said regression coefficient value is based upon the level of α2-MG in said population of liver fibrosis patients;
   $x_3$ is the concentration level of α2-MG; and wherein said formula is:

$$\text{Index Value} = \frac{\text{Exp}^{[-4.3633+(0.0108*HA\ ng/ml)+(0.0015*TIMP\text{-}1\ ng/ml)+(0.5357*\alpha 2\text{-}MG\ mg/ml)]}}{1+\text{Exp}^{[-4.3633+(0.0108*HA\ ng/ml)+(0.0015*TIMP\text{-}1\ ng/ml)+(0.5357*\alpha 2\text{-}MG\ mg/ml)]}};$$

(e) comparing the index value calculated for the individual to an index cutoff value, wherein said index cutoff value is between 0.2 and 0.7; and
   (f) determining the presence or severity of liver fibrosis in said individual based upon whether the index value is above or below the index cutoff value.

2. The method of claim 1, wherein the index cutoff value is between 0.3 and 0.6.

3. The method of claim 1, wherein an index value greater than 0.42 correlates with moderate or severe liver fibrosis.

4. The method of claim 1, wherein said individual has viral hepatitis.

5. The method of claim 4, wherein said individual is infected with hepatitis C virus.

6. The method of claim 4, wherein said individual is infected with hepatitis B virus.

7. The method of claim 4, wherein said individual is infected with hepatitis A virus.

8. The method of claim 4, wherein said individual is co-infected with at least two viruses.

9. The method of claim 8, wherein one of the viruses is selected from the group consisting of hepatitis A, hepatitis B, and hepatitis C.

10. The method of claim 1, wherein the level of α2-MG protein is determined using an anti-α2-MG antibody.

11. The method of claim 1, wherein step (a) comprises determining a level of α2-MG activity.

12. The method of claim 1, wherein the level of HA is determined using an HA-binding protein.

13. The method of claim 12, wherein the level of HA is determined using an anti-HA antibody.

14. The method of claim 1, wherein the level of TIMP-1 protein is determined using an anti-TIMP-1 antibody.

15. The method of claim 1, wherein step (c) comprises determining a level of TIMP-1 activity.

16. The method of claim 1, wherein the level of α2-MG protein, HA and TIMP-1 protein each is determined using an enzyme-linked assay.

17. The method of claim 1, wherein a single sample is obtained from said individual.

18. The method of claim 17, wherein said sample is selected from the group consisting of blood, serum, plasma, urine, saliva, and liver tissue.

19. The method of claim 18, wherein said sample is a serum sample.

20. The method of claim 1, comprising differentiating no or mild liver fibrosis from moderate to severe liver fibrosis.

21. A method for monitoring the efficacy of anti-fibrotic therapy in a patient, the method comprising:
   (a) determining a level of α2-macroglobulin (α2-MG) in a sample from a patient administered an anti-fibrotic therapy by contacting said sample with an α2-MG-specific binding agent;
   (b) determining a level of hyaluronic acid (HA) in a sample from said patient by contacting said sample with an HA-specific binding agent;
   (c) determining a level of tissue inhibitor of metalloproteinases-1 (TIMP-1) in a sample from said patient by contacting said sample with a TIMP-1-specific binding agent;
   (d) calculating an index value for said patient using a regression algorithm based upon said level of α2-MG, HA, and TIMP-1, wherein said regression algorithm has the a formula:

Index Value=Exp($b_0+b_1*x_1+b_2*x_2+b_3*x_3$)/(1Exp($b_0+b_1*x_1+b_2*x_2+b_3*x_3$)), wherein
- $b_0$ is an intercept value, wherein said intercept value is based upon the levels of α2-MG, HA, and TIMP-1 in a population of liver fibrosis patients;
- $b_1$ is a regression coefficient value for HA, wherein said regression coefficient value is based upon the level of HA in said population of liver fibrosis patients;
- $x_1$ is the concentration level of HA;
- $b_2$ is a regression coefficient value for TIMP-1, wherein said regression coefficient value is based upon the level of TEMP-1 in said population of liver fibrosis patients;
- $x_2$ is the concentration level of TIMP-1;
- $b_3$ is a regression coefficient value for α2-MG, wherein said regression coefficient value is based upon the level of α2-MG in said population of liver fibrosis patients;
- $x_3$ is the concentration level of α2-MG, wherein said formula is:

Index Value =

$$\frac{\mathrm{Exp}^{[-4.3633+(0.0108*HA\ ng/ml)+(0.0015*TIMP\text{-}1\ ng/ml)+(0.5357*\alpha 2\text{-}MG\ mg/ml)]}}{1+\mathrm{Exp}^{[-4.3633+(0.0108*HA\ ng/ml)+(0.0015*TIMP\text{-}1\ ng/ml)+(0.5357*\alpha 2\text{-}MG\ mg/ml)]}};$$

(e) comparing the index value calculated for the individual to an index cutoff value, wherein said index cutoff value is between 0.2 and 0.7; and (f) determining the presence or severity of liver fibrosis in said patient based upon whether the index value is above or below the index cutoff value, thereby monitoring the efficacy of anti-fibrotic therapy.

22. The method of claim 21, further comprising comparing the presence or severity of liver fibrosis determined in step (e) to the presence or severity of liver fibrosis in said patient at an earlier time.

23. The method of claim 21, wherein the level of α2-MG protein is determined using an anti-α2-MG antibody.

24. The method of claim 21, wherein the level of TIMP-1 protein is determined using an anti-TIMP-1 antibody.

25. A method of differentiating no or mild liver fibrosis from moderate/severe liver fibrosis in an individual, the method comprising:

(a) determining a level of α2-macroglobulin (α2-MG) in a sample from said individual by contacting said sample with an α2-MG-specific binding agent;

(b) determining a level of hyaluronic acid (HA) in a sample from said individual by contacting said sample with an HA-specific binding agent;

(c) determining a level of tissue inhibitor of metalloproteinases-1 (TIMP-1) in a sample from said individual by contacting said sample with a TIMP--specific binding agent;

(d) calculating an index value for the individual using a regression algorithm based upon said level of α2-MG, HA, and TIMP-1, wherein said regression algorithm has following a formula:

Index Value=$\mathrm{Exp}(b_0+b_1*x_1+b_2*x_2+b_3*x_3)/(1+\mathrm{Exp}(b_0+b_1*x_1+b_2*x_2+b_3*x_3))$ wherein
- $b_0$ is an intercept value, wherein said intercept value is based upon the levels of α2-MG, HA, and TIMP-1 in a population of liver fibrosis patients;
- $b_1$ is a regression coefficient value for HA, wherein said regression coefficient value is based upon the level of HA in said population of liver fibrosis patients;
- $x_1$ is the concentration level of HA;
- $b_2$ is a regression coefficient value for TIMP-1, wherein said regression coefficient value is based upon the level of TIMP-1 in said population of liver fibrosis patients;
- $x_2$ is the concentration level of TIMP-1;
- $b_3$ is a regression coefficient value for α2-MG, wherein said regression coefficient value is based upon the level of α2-MG in said population of liver fibrosis patients;
- $x_3$ is the concentration level of α2-MG, wherein said formula is:

Index Value =

$$\frac{\mathrm{Exp}^{[-4.3633+(0.0108*HA\ ng/ml)+(0.0015*TIMP\text{-}1\ ng/ml)+(0.5357*\alpha 2\text{-}MG\ mg/ml)]}}{1+\mathrm{Exp}^{[-4.3633+(0.0108*HA\ ng/ml)+(0.0015*TIMP\text{-}1\ ng/ml)+(0.5357*\alpha 2\text{-}MG\ mg/ml)]}};$$

and (e) diagnosing said individual as having no or mild liver fibrosis when the index value is below an index cutoff value of 0.42 and diagnosing said individual as having moderate or severe liver fibrosis when the index value is above the index cutoff value of 0.42.

26. The method of claim 25, wherein said individual has a disorder selected from the group consisting of viral hepatitis, autoimmune liver disease, alcoholic liver disease, fatty liver disease and drug-induced liver disease.

27. The method of claim 26, wherein said individual is infected with a virus selected from hepatitis A, hepatitis B, and hepatitis C virus.

28. The method of claim 25, wherein said samples are independently selected from the group consisting of blood, serum, plasma, urine, saliva and liver tissue.

29. The method of claim 28, wherein said level of α2-MG, HA and TIMP-1 each is determined in a serum sample.

30. A method for monitoring the progression of liver fibrosis in an individual, the method comprising:

(a) determining a level of α2-macroglobulin (α2-MG) in a sample from said individual by contacting said sample with an α2-MG-specific binding agent;

(b) determining a level of hyaluronic acid (HA) in a sample from said individual by contacting said sample with an HA-specific binding agent;

(c) determining a level of tissue inhibitor of metalloproteinases- 1 (TIMP-1) in a sample from said individual by contacting said sample with a TIMP-1-specific binding agent;

(d) calculating an index value for the individual using a regression algorithm based upon said level of α2-MG, HA, and TIMP-1, wherein said regression algorithm has a formula:

Index Value=$\mathrm{Exp}(b_0+b_1*x_1+b_2*x_2+b_3*x_3)/(1\mathrm{Exp}(b_0+b_1*x_1+b_2*x_2+b_3*x_3))$, wherein
- $b_0$ is an intercept value, wherein said intercept value is based upon the levels of α2-MG, HA, and TIMP-1 in a population of liver fibrosis patients;
- $b_1$ is a regression coefficient value for HA, wherein said regression coefficient value is based upon the level of HA in said population of liver fibrosis patients;
- $x_1$ is the concentration level of HA;

$b_2$ is a regression coefficient value for TIMP-1, wherein said regression coefficient value is based upon the level of TIMP-1 in said population of liver fibrosis patients;

$x_2$ is the concentration level of TIMP-1;

$b_3$ is a regression coefficient value for α2-MG, wherein said regression coefficient value is based upon the level of α2-MG in said population of liver fibrosis patients;

$x_3$ is the concentration level of α2-MG, wherein said formula is:

Index Value =

$$\frac{\text{Exp}^{[-4.3633+(0.0108*HA\ ng/ml)+(0.0015*TIMP\text{-}1\ ng/ml)+(0.5357*\alpha2\text{-}MG\ mg/ml)]}}{1+\text{Exp}^{[-4.3633+(0.0108*HA\ ng/ml)+(0.0015*TIMP\text{-}1\ ng/ml)+(0.5357*\alpha2\text{-}MG\ mg/ml)]}};$$

(e) comparing the index value calculated for the individual to an index cutoff value, wherein said index cutoff value is between 0.2 and 0.7; and (f) determining the presence or severity of liver fibrosis in said individual based upon whether the index value is above or below the index cutoff value to monitor progression.

31. The method of claim 30, further comprising comparing the presence or severity of liver fibrosis determined in step (e) to the presence or severity of liver fibrosis in said individual at an earlier time.

32. The method of claim 30, comprising determining the levels of at most three markers of fibrosis.

33. The method of claim 30, comprising determining the levels of at least three markers of fibrosis.

34. The method of claim 30, wherein the level of α2-MG protein is determined using an anti-α2-MG antibody.

35. The method of claim 30, wherein the level of TIMP-1 protein is determined using an anti-TIMP-1 antibody.

36. A method of monitoring a response to a therapeutic agent in an individual in need of such agent, the method comprising:

(a) determining a level of α2-macroglobulin (α2-MG) in a sample from said individual by contacting said sample with an α2-MG-specific binding agent;

(b) determining a level of hyaluronic acid (HA) in a sample from said individual by contacting said sample with an HA-specific binding agent;

(c) determining a level of tissue inhibitor of metalloproteinases-1 (TIMP-1) in a sample from said individual by contacting said sample with a TIMP-1-specific binding agent;

(d) calculating an index value for the individual using a regression algorithm based upon said level of α2-MG, HA, and TIMP-1, wherein said regression algorithm has following a formula:

Index Value=$\text{Exp}(b_0+b_1*x_1+b_2*x_2+b_3*x_3)/(1\text{Exp}(b_0+b_1*x_1+b_2*x_2+b_3*x_3))$, wherein $b_0$ is an intercept value, wherein said intercept value is based upon the levels of α2-MG, HA, and TIMP-1 in a population of liver fibrosis patients;

$b_1$ is a regression coefficient value for HA, wherein said regression coefficient value is based upon the level of HA in said population of liver fibrosis patients;

$x_1$ is the concentration level of HA;

$b_2$ is a regression coefficient value for TIMP-1, wherein said regression coefficient value is based upon the level of TIMP-1 in said population of liver fibrosis patients;

$x_2$ is the concentration level of TIMP-1;

$b_3$ is a regression coefficient value for α2-MG, wherein said regression coefficient value is based upon the level of α2-MG in said population of liver fibrosis patients;

$x_3$ is the concentration level of α2-MG, wherein said formula is:

Index Value =

$$\frac{\text{Exp}^{[-4.3633+(0.0108*HA\ ng/ml)+(0.0015*TIMP\text{-}1\ ng/ml)+(0.5357*\alpha2\text{-}MG\ mg/ml)]}}{1+\text{Exp}^{[-4.3633+(0.0108*HA\ ng/ml)+(0.0015*TIMP\text{-}1\ ng/ml)+(0.5357*\alpha2\text{-}MG\ mg/ml)]}};$$

(e) comparing the index value calculated for the individual to an index cutoff value, wherein said index cutoff value is between 0.2 and 0.7; and (f) determining the presence or severity of liver fibrosis in said individual based upon whether the index value is above or below the index cutoff value to monitor response.

37. The method of claim 36, further comprising comparing the presence or severity of liver fibrosis determined in step (e) to the presence or severity of liver fibrosis in said individual at an earlier time.

38. The method of claim 36, wherein the level of α2-MG protein is determined using an anti-α2-MG antibody.

39. The method of claim 36, wherein the level of TIMP-1 protein is determined using an anti-TIMP-1 antibody.

40. The method of claim 36, wherein the individual has a viral disease.

41. The method of claim 40, wherein the viral disease is selected from the group consisting of hepatitis A, hepatitis B, and hepatitis C.

42. The method of claim 36, wherein the therapeutic agent is an anti-fibrotic agent.

43. The method of claim 36, wherein the therapeutic agent is an anti-viral agent.

44. The method of claim 1, wherein said individual is diagnosed as having no or mild liver fibrosis when the index value is less than the index cut-off value.

45. The method of claim 1, wherein said individual is diagnosed as having moderate or severe liver fibrosis when the index value is greater than the index cut-off value.

46. The method of claim 1, wherein said regression algorithm uses logistic or linear regression.

* * * * *

UNITED STATES PATENT AND TRADEMARK OFFICE
CERTIFICATE OF CORRECTION

PATENT NO. : 7,670,764 B2  Page 1 of 1
APPLICATION NO. : 10/971195
DATED : March 2, 2010
INVENTOR(S) : Esther H. Oh et al.

It is certified that error appears in the above-identified patent and that said Letters Patent is hereby corrected as shown below:

Claim 21, Column 46, lines 65-67:
"the a formula:
  Index Value = $Exp(b_0 + b_1 * x_1 + b_2 * x_2 + b_3 * x_3) / (1 Exp(b_0 + b_1 * x_1 + b_2 * x_2 + b_3 * x_3))$,"

should read:
-- a formula:
  Index Value = $Exp(b_0 + b_1 * x_1 + b_2 * x_2 + b_3 * x_3) / (1 + Exp(b_0 + b_1 * x_1 + b_2 * x_2 + b_3 * x_3))$, --

Claim 21, Column 47, line 11:
"of TEMP-1 in said population of liver fibrosis patients;"

should read:
-- of TIMP-1 in said population of liver fibrosis patients; --

Claim 25, Column 47, line 44:
"from moderate/severe liver fibrosis in an individual, the"

should read:
-- from moderate or severe liver fibrosis in an individual, the --

Claim 30, Column 48, line 57:
"Index Value = $Exp(b_0 + b_1 * x_1 + b_2 * x_2 + b_3 * x_3) / (1 Exp(b_0 +$"

should read:
-- Index Value = $Exp(b_0 + b_1 * x_1 + b_2 * x_2 + b_3 * x_3) / (1 + Exp(b_0 +$ --

Signed and Sealed this

Fourth Day of May, 2010

David J. Kappos
*Director of the United States Patent and Trademark Office*